US006248525B1

(12) United States Patent
Nilsen

(10) Patent No.: US 6,248,525 B1
(45) Date of Patent: Jun. 19, 2001

(54) METHOD FOR IDENTIFYING ESSENTIAL OR FUNCTIONAL GENES

(75) Inventor: Timothy W. Nilsen, Russell, OH (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/196,523

(22) Filed: Nov. 20, 1998

Related U.S. Application Data

(60) Provisional application No. 60/079,851, filed on Mar. 30, 1998.

(51) Int. Cl.[7] .............................. C12Q 1/68; C07H 21/04; C12N 15/63; C12N 15/74; C12N 5/00

(52) U.S. Cl. .............................. 435/6; 435/243; 435/325; 435/455; 435/471; 536/23.1; 536/24.5

(58) Field of Search ................................. 536/23.1, 24.5; 435/6, 455, 471, 325, 243

(56) References Cited

U.S. PATENT DOCUMENTS

| | | |
|---|---|---|
| 4,987,071 | 1/1991 | Cech et al. . |
| 5,168,053 | 12/1992 | Altman et al. . |
| 5,225,337 | 7/1993 | Robertson et al. . |
| 5,254,678 | 10/1993 | Haseloff et al. . |
| 5,334,711 | 8/1994 | Sproat et al. . |
| 5,496,698 | 3/1996 | Draper et al. . |
| 5,525,468 | 6/1996 | McSwiggen . |
| 5,527,895 | 6/1996 | Hampel et al. . |
| 5,580,967 | 12/1996 | Joyce . |
| 5,624,824 | 4/1997 | Yuan et al. . |

FOREIGN PATENT DOCUMENTS

| | | |
|---|---|---|
| 321021 | 5/1991 | (EP) . |
| WO88/04300 | 6/1988 | (WO) . |
| WO89/05852 | 6/1989 | (WO) . |
| WO91/04324 | 4/1991 | (WO) . |
| WO91/94319 | 4/1991 | (WO) . |
| WO92/03566 | 3/1992 | (WO) . |
| WO93/22434 | 11/1993 | (WO) . |
| WO94/13791 | 6/1994 | (WO) . |
| WO95/24489 | 9/1995 | (WO) . |
| WO96/18733 | 6/1996 | (WO) . |
| WO96/21731 | 7/1996 | (WO) . |
| WO97/10360 | 3/1997 | (WO) . |
| WO97/18312 | 5/1997 | (WO) . |
| WO97/33991 | 9/1997 | (WO) . |
| WO98/06837 | 2/1998 | (WO) . |
| WO98/32880 | 7/1998 | (WO) . |

OTHER PUBLICATIONS

Agrawal, et al., "Oligodeoxynucleoside phosphoramidates and phosphorothioates as inhibitors of human immunodeficiency virus," *Proc. Natl. Acad. Sci. USA* 85(19):7079–7083 (1988).
Agrawal, et al., "Mixed backbone oligonucleotides: improvement in oligonucleotide–induced toxicity in vivo," *Antisense Nucleic Acid Drug Dev* 8(2):135–9 (1998).
Akhtar, "Antisense technology: selection and delivery of optimally acting antisense oligonucleotides," *J Drug Target.* 5(4):225–34 (1998).
Altman, "RNA Enzyme–Directed Gene Therapy," *Proc. Nat. Acad. Sci. USA* 90:10898–10900 (1993).
Buzayan et al., "Satellite tobacco ringspot virus RNA: A subset of the RNA sequence is sufficient for autolytic processing" *Proc. Natl. Acad. Sci. USA* 83:8859–8862 (1968).
Cech, "Self–Splicing Of Group I Introns," *Annu. Rev. Biochem.* 59:543–568 (1990).
Chalfie, et al., "Green Fluorescent Protein as a Marker for Gene Expressions" *Science* 263:802–805 (1994).
Cormack, et al., "FACS–optimized Mutants of the Green Fluorescent Protein (GFP)," *Gene* 173:33–38 (1996).
Crooke, "An overview of progress in antisense therapeutics," *Antisense Nucleic Acid Drug Dev* 8(2):115–22 (1998).
Crooke, "Molecular mechanisms of antisense drugs: RNase H," *Antisense Nucleic Acid Drug Dev* 8(2):133–4 (1998).
Crooke, "Antisense therapeutics," *Biotechnol Genet Eng Rev* 15:121–57 (1998).
Forster, et al., "External Guide Sequences For An RNA Enzyme," *Science* 249:783–786 (1990).
Giles, et al., "Increased specificity for oligodeoxynucleotide targeting of RNA cleavage by RNase H using chimeric methylphosphonodiester/phosphodiester structures," *Nucleic Acid Res.* 20:763 (1992).

(List continued on next page.)

*Primary Examiner*—David Guzo
*Assistant Examiner*—Gerald G Leffers, Jr.
(74) *Attorney, Agent, or Firm*—Arnall Golden Gregory LLP

(57) ABSTRACT

Two methodologies are provided: the first provides a means for rapidly and efficiently identifying essential and functional genes; and the second provides a means for obtaining biologically active nucleic molecules (ribozymes, EGSs, and antisense,) which can be used to inactivate functional genes. In the first method, a library of EGSs is prepared based on all possible known compositions. In a preferred embodiment, the EGSs are twelve or thirteen-mers for targeting bacterial RNAse to cleave a substrate. This library is added to the cells containing the genes to be screened, for example, *E. coli*. Those cells in which the EGS causes a loss of viability, or other phenotype, are identified. The EGS(s) responsible for the loss of viability are analyzed, and the resulting sequence information used to identify the gene within the known genomic sequences. In the second method, nucleotide molecules with optimal biological activity, for example, directing cleavage of a gene of interest by RNase P, are rapidly identified through the use of a vector including two reporter genes, the first in phase with the gene of interest, and the second as a control to verify that the vector is present in a cell or to aid in selection of cells containing the vector. Those cells where the gene of interest is cleaved by the functional oligonucleotide molecule can then be identified by reference to reporter gene 1. The responsible functional oligonucleotide molecules is then isolated and characterized.

17 Claims, 11 Drawing Sheets

OTHER PUBLICATIONS

Graham, et al., "Characteristics of a Human Cell Line Transformed by DNA from Human Adenovirus Type 5," *J. Gen Virol.* 36:59–72 (1977).

Guerrier–Takeda, et al., "Phenotypic conversion of drug–resistant bacteria to a drug sensitivity," *Proc. Natl. Acad. USA* 94:8468–8472 (1997).

Haseloff, et al., "Simple RNA Enzymes with New and Highly Specific Endoribonuclease Activities," *Nature* 334:585–591 (1988).

Kawasaki et al., "Selection of the best target site for ribozyme–mediated cleavage within a fusion gene for adenovirus E1A–associated 300 kDa protein (p300) and luciferase," *Nucl. Acids Res.* 24(15):3010–3016 (1996).

Lieber, et al., "Selection of Efficient Cleavage Sites in Target RNAs by Using a Ribozyme Expression Library," *Mol. Cell. Biol.* 8:466–472 (1995).

Liu and Altman, "Inhibition of Viral Gene Expression by the Catalytic RNA Subunit of RNase P from *Escherichia coli,*" *Genes Dev.* 9:471–480 (1995).

Mather, "Establishment and Characterization of Two Distinct Mouse Testicular Epithelial Cell Lines," *Biol. Reprod.* 23:243–252 (1980).

Mather, et al., "Culture of Testicular Cells in Hormone–Supplemented Serum–Free Medium," *Annals N. Y. Acad. Sci* 383:44–68 (1982).

Mizuno, et al., "A unique mechanism regulating gene expression: translational inhibition by a complementary RNA transcript (micRNA)," *Proc. Natl. Acad. Sci. USA* 81(7): 1966–70(1984).

Stein, "How to design an antisense oligodeoxynucleotide experiment: a consensus approach," *Antisense Nucleic Acid Drug Dev* 8(2):129–32 (1998).

Urlaub, et al., "Isolation of Chinese hamster cell mutants deficient in dihydrofolate reductase activity" *Proc. Natl. Acad. Sci. USA* 77:4216 (1980).

Yuan, et al., "Targeted cleavage of mRNA by human RNase P," *Proc. Natl. Acad. Sci. USA* 89:8006–8010 (1992).

Zamecnik, et al., "Inhibition of Rous sarcoma virus replication and cell transformation by a specific oligodeoxynucleotide", *Proc. Natl. Sci. USA* 75: 280–284 (1978).

Zolotukhin, et al., "A 'Humanized' Green Fluorescent Protein cDNA Adapted for High–Level Expression in Mammalian Cells," *J. Virol* 70:4646–4654 (1996).

Zoumadakis and Tabler, "Comparative Analysis of cleavage Rates After Systematic Permutation of the NUX1 Consensus Target Motif for Hammerhead Ribozymes," *Nucl. Acids Res.* 23:1192–1196 (1995).

Guerrier–Takada, et al., "Artificial regulation of gene expression in *Escherichia coli* by RNase P" *Proc. Natl. Acad. Sci. U.S.A.* 92:11115–11119 (1995).

Yuan & Altman, "Selection of guide sequences that direct efficient cleavage of mRNA by Human Ribonuclease P," *Science* 263:1269–1273 (1994).

Parental expression construct: pBAD Guzman, Belin, Carlson & Beckwith (1995) J. Bacteriol. 177, 4121

| EGS library | theoretical complexity |
|---|---|
| $N_{12}$ CACCA | $1.6 \times 10^7$ |
| $N_{11}$ CCACCA | $4.2 \times 10^6$ |

METHOD FOR IDENTIFYING ESSENTIAL OR FUNCTIONAL GENES

CROSS REFERENCE TO RELATED APPLICATION

This application claims priority to U.S. patent application Ser. No. 60/079,851 filed Mar. 30, 1998, by Timothy W. Nilsen.

BACKGROUND OF THE INVENTION

This is generally in the field of biologically active nucleic acid molecules, such as EGSs, ribozymes, and antisense RNA, and in the broad field of functional analysis of complex genomes, and more specifically, the use of biologically active nucleic acids (RNAS) to specifically downmodulate the expression of messenger RNAs that encode proteins essential for viability.

Recent advances in automated DNA sequencing technologies and their application to the genomes of multiple organisms have resulted in the accumulation of a vast amount of nucleotide sequence information. At present, the genomic sequences of sixteen bacteria, including several important pathogens, most recently the causative agents of tuberculosis and syphilis, have been determined in their entirety. In addition, the complete sequence of a "simple" eukaryote (*Saccharomyces cerevisiae*) is known and a similar analysis of the nematode *C. elegans* will be released shortly. It is likely that many more genomic sequences, both prokaryotic and eukaryotic, will be revealed in the near term.

A major challenge involves the functional analysis of the available and forthcoming genomic information; i.e. determination of the biological role of genes revealed by sequencing. It is particularly important to identify those genes that encode proteins essential for viability. Such proteins are of clear significance in the development of effective chemotherapeutic agents targeted to pathogenic organisms. Currently, there are several strategies available, alone or in combination, for functional genomic analysis, including bioinformatics, expression analysis, and targeted gene disruption. Informatics alone is unlikely to provide definitive new insight into gene function. For example, although *E. coli* is the best studied organism by far, the genomic sequence revealed that approximately forty percent of the genes were of unknown function. Expression profiling provides primarily inferential information, and targeted gene disruption, although definitive, is labor intensive and time consuming.

Accordingly, it is highly desirable to have a robust, high throughput method that identifies all or most essential genes in a particular organism.

It is therefore an object of the present invention to provide an efficient method and compositions for the identification of genes in bacteria and eukaryotic cells that encode proteins essential for survival.

It is a further object of the present invention to provide methods and compositions for reducing or inactivating expression of such genes.

Ribonucleic acid (RNA) molecules can serve not only as carriers of genetic information, for example, genomic retroviral RNA and messenger RNA (mRNA) molecules and as structures essential for protein synthesis, for example, transfer RNA (tRNA) and ribosomal RNA (rRNA) molecules, but also as enzymes which specifically cleave nucleic acid molecules. Such catalytic RNA molecules are called ribozymes. Although ribozymes theoretically can cleave any desired site in an RNA molecule, in reality not all sites are efficiently cleaved by ribozymes designed to cleave them. This is especially true in vivo where numerous examples have been described of sites that are inefficiently cleaved by targeted ribozymes. The problem is not a total lack of sites in an RNA molecule of interest, but rather determining which sites, among the many possible sites, can be cleaved most efficiently. This is important since it is often desirable to identify the most efficient sites of cleavage and not just any site that can be cleaved. The process of targeting one or a few sites on an RNA molecule essentially at random and then testing for cleavage is not likely to identify the most efficient sites. Comprehensive testing of all sites is not practical because of the amount of labor involved in making and testing each ribozyme or external guide sequence ("EGS"). WO 96/21731 by Innovir describes selection of efficiently cleaved sites in this manner by making and testing 80 different EGSs targeted to different sites. However, this represented only a fraction of the possible sites. Techniques using similar labor intensive methods for identifying sites that are accessible for cleavage are described in U.S. Pat. Nos. 5,525,468 and 5,496,698.

Kawasaki et al., *Nucl. Acids Res.* 24(15):3010–3016 (1996), describes the use of a transcript encoding a fusion between adenovirus E1A-associated 300 kDa protein (p300) and luciferase to assess the efficiency with which sites in the p300 RNA are cleaved by hammerhead ribozymes in vivo. A few hammerhead ribozymes targeted to sites having GUX triplets (which are required for cleavage by a hammerhead ribozyme) were designed and expressed from a vector in cells. A separate vector expressed the p300-luciferase fusion RNA. Cleavage of sites in the p300 portion of the transcript was assessed by measuring luciferase activity. Kawasaki et al. tested each ribozyme separately and therefore their method also does not solve the need for a rapid, efficient selection process.

As an alternative to actually testing for individual cleavable sites, or preliminary to such testing, attempts have also been made to predict which sites will be accessible from theoretical considerations or by empirically testing the presence or absence of secondary or tertiary structure at sites in RNA molecules. For example, Ruffner et al., *Biochemistry* 29:10695–10702 (1990), Zoumadakis and Tabler, *Nucl. Acids Res.* 23:1192–1196 (1995), Shimayama et al., Biochemistry 34:3649–3654 (1995), Haseloff and Gerlach, *Nature* 334:585–591 (1988), and Lieber and Strauss, *Mol. Cell. Biol.* 8:466–472 (1995), describe attempts to use rules of structure formation in RNA to predict cleavable sites. However, the structure of RNA molecules cannot be accurately predicted from theoretical considerations and the determination of actual secondary and tertiary structure of an RNA molecule requires extensive experimentation. It can also be difficult to identify ribozymes and other biologically active molecules that will function inside cells since not all such biologically active molecules that are functional in vitro are functional in cells because they are, for example, improperly localized, sequestered, or bound by intracellular proteins.

It is therefore an object of the present invention to provide a method and compositions for identifying biologically active RNA molecules, such as ribozymes, EGSs for ribozymes, and antisense RNA, that alter expression of an RNA molecule efficiently in vivo.

It is a further object of the present invention to provide a method and compositions for identifying sites in an RNA, or nucleotide molecules involved in expression of a target RNA, that are most accessible as target sites for alteration of expression in vivo.

It is a further object of the present invention to provide functional oligonucleotide molecules directed to sites identified as accessible.

SUMMARY OF THE INVENTION

Two methodologies are provided: the first provides a means for rapidly and efficiently identifying essential and functional genes; and the second provides a means for obtaining biologically active nucleotide molecules (ribozymes, EGSs, and antisense), which can be used to inactivate functional genes.

In the first method, a library of EGSs is prepared based on all possible known compositions. This is readily calculated knowing the minimum sequence requirements required for targeting and cleavage by RNase P and the length of the EGS based on the predicted size of the genome to be screened. In a preferred embodiment, the EGSs are twelve or thirteen-mers for targeting bacterial RNase P to cleave a substrate. This library of EGSs is added to the cells containing the genes to be screened, for example, E. coli. Additional methods may be used to amplify the library, or the cells which survive exposure to the EGSs. Those cells in which the EGS causes a loss of viability, or other phenotype, are identified. The EGS(s) responsible for the loss of viability are analyzed, and the resulting sequence information used to identify the gene within the known genomic sequences.

In the second method, nucleotide molecules with optimal biological activity, for example, directing cleavage of a gene of interest by RNase P, are rapidly identified through the use of a vector including two reporter genes, the first in frame with the gene of interest, and the second as a control to verify that the vector is present in a cell or to aid in selection of cells containing the vector. For example, the vector may include a gene encoding any protein that confers drug resistance in a bacteria (the gene of interest) in frame with a beta-galactosidase gene (reporter gene 1) and a gene encoding antibiotic resistance (reporter gene 2). In the preferred embodiment, the vector also includes one of many possible functional oligonucleotide molecules (such as an EGS), although this can also be provided on a separate vector. The vector(s) is added to cells such as E. coli. The cells containing the vectors can be isolated by treatment with the antibiotic that kills all the cells that do not express the gene for antibiotic resistance. Those cells where the gene of interest is cleaved by the functional oligonucleotide molecule can then be identified by reference to reporter gene 1. Those cells which are identified can then be amplified. In one preferred embodiment, the gene of interest is essential for viability. In this case, the plate with the bacteria is first replicated, then the cells which are killed by cleavage of the mRNA of interest are identified, and the responsible functional oligonucleotide molecules isolated from the duplicate plate.

These methods provide powerful tools for identifying essential genes whose sequence is known only as part of a genome with unknown function, as well as means for identifying functional oligonucleotide molecules, useful as diagnostic reagents and therapeutics.

DETAILED DESCRIPTION OF THE INVENTION

Figure 1:
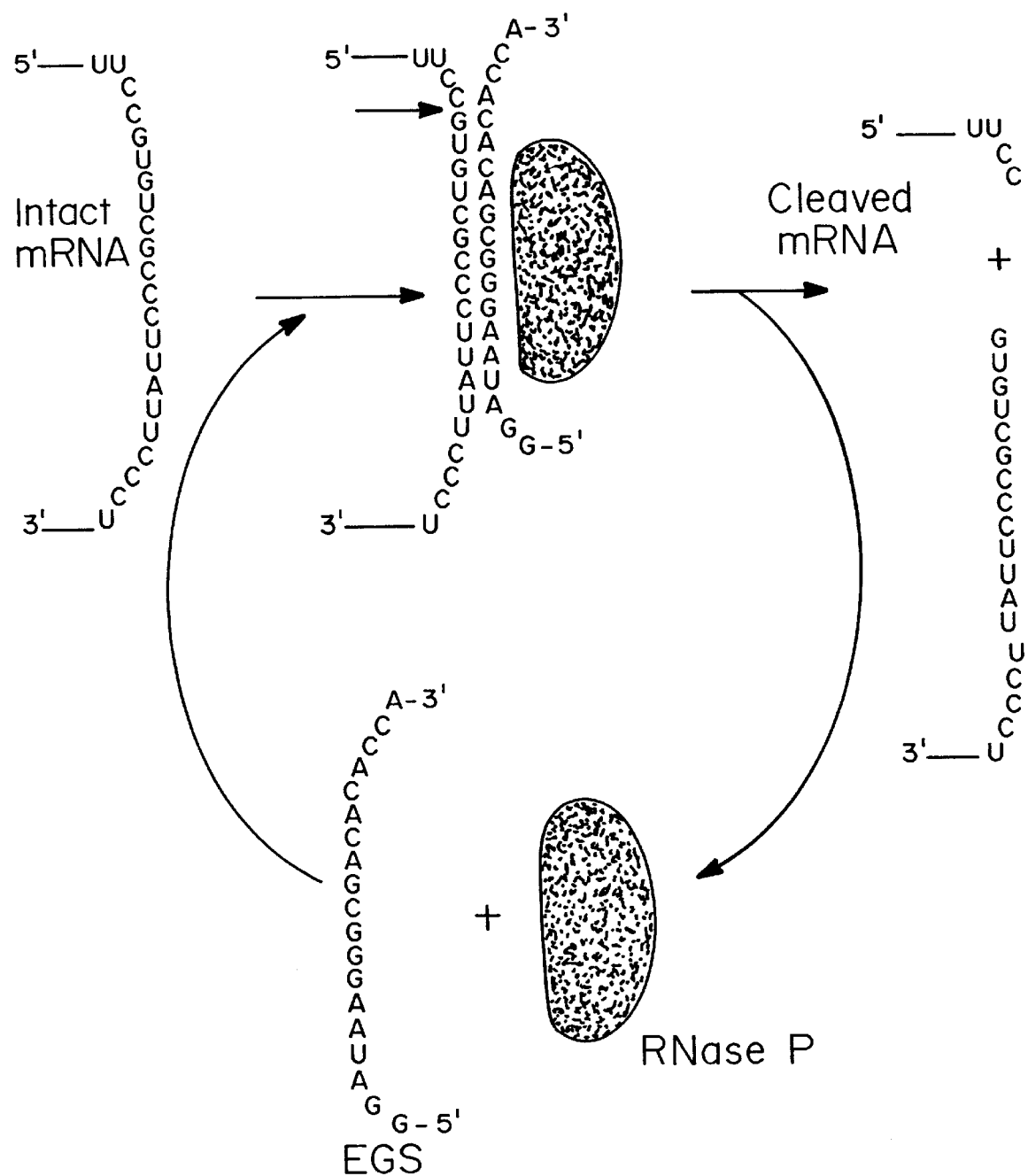
FIG. 1 is a diagram of the mechanism of action of EGSs (SEQ ID NO:1) on cleavage of target mRNAs (SEQ ID NO:2).

There are two general methods described, the first for identification of essential or functional genes in a known genome using EGSs, and the second for identifying functional oligonucleotide molecules, including EGSs, ribozymes and antisense, which are active on a desired RNA molecule. In the preferred embodiment of the latter method, the functional oligonucleotide molecules are EGSs and the desired RNA molecule is the RNA transcribed from a known gene.

I. Definitions and General Elements of the Methods and Reagents

Ribonucleic acid (RNA) molecules can serve not only as carriers of genetic information, for example, genomic retroviral RNA and messenger RNA (mRNA) molecules and as structures essential for protein synthesis, for example, transfer RNA (tRNA) and ribosomal RNA (rRNA) molecules, but also as enzymes which specifically cleave nucleic acid molecules or as elements which direct an enzyme which specifically cleaves nucleic acid molecules. Any of these RNAs can be a target for cleavage or inactivation by a functional oligonucleotide molecule.

A key advantage of the disclosed methods and vectors is the assessment of alteration of expression of an RNA of interest in an in vivo setting which will be the same or similar to the setting where identified functional oligonucleotide molecules, or affect or oligomers based on such identified RNA molecules, will be used. Another advantage of the disclosed methods is that all, or a substantial number, of the accessible sites in the RNA of interest can be determined in one assay. Such sites, determined to be accessible for one type of functional oligonucleotide molecule, may be accessible for other types of functional oligonucleotide molecules. In the case of ribozymes and EGSs, the disclosed methods allow assessment not just of cleavage of the RNA of interest, but also of an ultimate desired phenotype (that is, loss of the phenotype supported by the RNA of interest) as a result of such cleavage.

A. RNA Molecules of Interest

The RNA molecule of interest can be any RNA molecule or portion of an RNA molecule that can be transcribed. It is preferred that the RNA molecule of interest be an RNA molecule involved in the expression of a gene of interest, the expression of which is to be inhibited. The RNA molecule can be a mRNA, a portion of a mRNA, a pre-mRNA including introns, or an intron. Alternatively the RNA molecule can be a viral RNA.

Important pathogens include the bacteria *Pseudomonas aeruginosa, Mycobacterium tuberculosis, Hemophilus influenzae, Staphylococcus aureus, Mycoplasma pneumoniae, Escherichia coli, Streptococcus pneumoniae, Neisseria gonorrhaoeae, Streptococcus viridans, Streptococcus pyogenes, Proteus mirabilis, Proteus vulgaris, Salmonella typhimnurium, Shigella dysentereae, Clostridium difficile,* and *Klebsiella pneumoniae,* and the fungi *Candida albicans, Aspergillus flavus, Aspergillus fumagatus,* and *Histoplasmatus capsulatum.*

B. Functional oligonucleotide molecules.

Functional nucleotide (typically an RNA) molecules are designed to alter, or preferably inhibit, the expression of an RNA of interest. These molecules can be ribozymes, EGSs for RNase P, or antisense RNA. Ribozymes and EGSs inhibit expression of an RNA molecule by cleaving or mediating cleavage of the RNA molecule at a targeted site. Antisense RNA or DNA inhibits expression of an RNA molecule through a sequence-specific interaction with the RNA molecule.

External Guide Sequences ("EGSs")

Any RNA sequence in a prokaryotic or eukaryotic cells can be converted into a substrate for RNase P. In bacterial cells, the substrate is created using an EGS having at its 5' terminus nucleotides complementary to the nucleotides 3' to the cleavage site in the RNA to be cleaved and at its 3' terminus the nucleotides NCCA (N is any nucleotide). This is described in U.S. Pat. No. 5,168,053, WO 92/03566 and Forster and Altman, *Science* 238:407–409 (1990).

EGS for promoting RNase P-mediated cleavage of RNA has also been developed for use in eukaryotic systems as described by U.S. Pat. No. 5,624,824, Yuan et al., *Proc. Natl. Acad. Sci. USA* 89:8006–8010 (1992), WO 93/22434, WO 95/24489, and WO 96/21731. As used herein, "external guide sequence" and "EGS" refer to any oligonucleotide or oligonucleotide analog that forms, in combination with a target RNA, a substrate for RNase P. EGS technology has been used successfully to decrease levels of gene expression in both bacteria (Altman et al. (1993)) and mammalian cells in tissue culture (Yuan et al., *Proc. Natl. Acad. Sci. USA* 89:8006–8010 (1992); Liu and Altman, *Genes Dev.* 9:471–480 (1995)).

The requirements for an EGS functional with prokaryotic RNase P are less stringent than those for a eukaryotic EGS. The critical elements of a prokaryotic EGS are (1) nucleotide sequence which specifically binds to the targeted RNA substrate to produce a short sequence of base pairs 3' to the cleavage site on the substrate RNA and (2) a terminal 3'-NCCA, where N is any nucleotide, preferably a purine. The sequence generally has no fewer than four, and more usually six to fifteen, nucleotides complementary to the targeted RNA. It is not critical that all nucleotides be complementary. The rate of cleavage is dependent on the RNase P, the secondary structure of the hybrid substrate, which includes the targeted RNA and the presence of the 3'-NCCA in the hybrid substrate. Eukaryotic EGSs also promote cleavage by prokaryotic RNase P and can be used for this purpose.

An EGS for promoting cleavage by eukaryotic RNase P, referred to herein as a eukaryotic EGS, contains sequences which are complementary to the target RNA and which forms secondary and tertiary structure akin to portions of a tRNA molecule. A preferred form of eukaryotic EGS contains at least seven nucleotides which base pair with the target sequence 3' to the intended cleavage site to form a structure like the amino acyl acceptor stem (A stem), nucleotides which base pair to form a stem and loop structure similar to the T stem and loop, followed by at least three nucleotides that base pair with the target sequence to form a structure like the dihydroxyuracil stem. Another preferred form of eukaryotic EGS, referred to herein as a Short External Guide Sequence (SEGS), provide a minimal structure recognized as a substrate by RNase P when hybridized to a target molecule. The SEGS/target RNA complex includes structures similar to the A stem and the T stem of a tRNA, the natural substrate of RNase P.

Ribozymes

Ribozymes include any trans-cleaving catalytic nucleic acid. Several classes of such ribozymes are known and have been either adapted or designed to cleave RNA molecules in a site-specific manner. Intron-derived ribozymes are derived from self-excising introns found in Tetrahymena RNA, as described in U.S. Pat. No. 4,987,071, WO 88/04300, and Cech, *Annu. Rev. Biochem.* 59:543–568 (1990). Hammerhead ribozymes are derived from self-cleaving RNA molecules present in certain viruses (Buzayan et al., *Proc. Natl. Acad. Sci. USA* 83:8859–8862 (1968); Forster and Symons, *Cell* 50:9–16 (1987)). Design of hammerhead ribozymes for the specific cleavage of target RNA molecules and their use is described in U.S. Pat. No. 5,254,678, WO 89/05852, EP 321021, and U.S. Pat. No. 5,334,711. Derivatives of hammerhead ribozymes are described in U.S. Pat. No. 5,334,711; WO 94/13789; and WO 97/18312. Axehead ribozymes are derived from self-cleaving domains in some viroid RNAs such as hepatitis delta virus (U.S. Pat. Nos. 5,527,895; 5,225,337, WO 91/04319, and WO 91/04324). Ribozymes can also be produced using in vitro evolution techniques (WO 95/24489 and U.S. Pat. No. 5,580,967).

Antisense

Antisense molecules are usually single stranded DNA or RNA molecules, or their substituted analogues, which can bind to the target RNA through Watson and Crick base pairing and prevent the translation of these RNAs (Stein C A, *Antisense Nucleic Acid Drug Dev* 8(2):129–32 (1998); Crooke S T, *Antisense Nucleic Acid Drug Dev* 8(2):115–22 (1998); Akhtar S, *J Drug Target.* 5(4):225–34 (1998); Mizuno, T., et al., *Proc. Natl. Acad. Sci. USA*, 81, (1983); Crooke S T, *Biotechnol Genet Eng Rev* 15:121–57 (1998); Zamecnik, in Prospects for Antisense Nucleic Acid Therapy of Cancer and Aids, ed., Wickstrom, Wiley-Liss, New York)). They are usually 15 to 30 nucleotides long and have been used widely to inhibit expression of various proteins (Zamecnick, P. C. and Stevenson, M. L. *Proc. Natl. Acad. Sci., USA*, 75, 280 (1978); Agrawal, S., *Proc. Natl. Acad. Sci., USA*, 85, 7089, (1988)). In addition to the inhibition of translation of the mRNA, DNA based antisense can also inhibit expression of proteins by presenting the DNA-RNA hybrid as a target for cleavage by the endogenous RNaseH enzyme (Crooke S T, *Antisense Nucleic Acid Drug Dev* 8(2):133–4 (1998); Caselmann et al., *Intervirology* 40(5–6):394–9 (1997); Giles, R. V. and Tidd, D. M., *Nucleic Acid Res.*, 20, 763 (1992)), thereby destroying the target RNA. The antisense molecules can be made more resistant to nucleases by introducing chemical modifications, such as 2' modifications and phosphorothioate diester linkages instead of the phosphodiester linkage (Agrawal S and Zhao Q, *Antisense Nucleic Acid Drug Dev* 8(2):135–9 (1998); Agrawal, S., et al, *Proc. Natl. Acad. Sci., USA*, 85, 7089, (1988)) and duplexes of these molecules with an RNA is recognized by RNaseH.

C. Vectors.

The disclosed methods use vectors which have certain elements in common, including reporter genes, genes for selection of cells which do, or do not, contain the functional oligonucleotide molecules, and the necessary sequences for expression and replication of the vectors. The disclosed vectors are generally of two forms, with each form adapted to either the assay for identifying essential and functional genes or the assay to identify functional oligonucleotide molecules. These are generally described as follows.

Vectors for Use in Identifying Essential or Functional Genes

Vectors for use in the method of identifying essential or functional genes encode a functional oligonucleotide molecule including a degenerate targeting sequence. By including the degenerate targeting sequence, the set of encoded functional oligonucleotide molecules include functional oligonucleotide molecules targeted to every possible sequence. The length of the targeting sequence is preferably chosen to match the length of unique sequences present in the genome of cells to be assayed. This relationship is described in more detail below. The effect is to obtain a set of vectors that collectively encode a set of functional oligonucleotide molecules targeted to every possible unique sequence in the genome of the cells of interest. The set of vectors is transformed or transfected into the cells, and the cells screened or selected for cell death or for a change in a phenotype of interest. The selected cells harbor the functional oligonucleotide molecules which are targeted to essential or functional genes in the cells. The functional oligonucleotide molecules can then be identified by characterizing the vectors in the cells. The genes targeted by the functional oligonucleotide molecules can be identified by correlating the targeting sequences in the functional oligonucleotide molecules with the known genomic sequences.

Vectors for Use in Identifying Functional oligonucleotide molecules

Vectors for use in functional oligonucleotide molecule assays include a reporter gene 1 encoding the fusion transcript including the RNA molecule of interest and RNA encoding reporter protein A. Inactivation of the RNA molecule of interest alters expression of the reporter protein A. The vectors also include a second reporter gene 2 encoding a second reporter protein B. Expression of the second reporter protein B can be used both to detect transformation or transfection of the vector into cells and as a control for effects on the expression of the first reporter protein that are not due to inhibition of expression of the RNA molecule of interest. The vector also encodes a functional oligonucleotide molecule targeted to the RNA of interest. The method preferably uses a set of these vectors where each vector in the set encodes a different functional oligonucleotide molecule, each targeted to a different site in the RNA molecule of interest. The set of vectors is transformed or transfected into appropriate cells, and the cells are screened or selected for expression of the second reporter protein B. The cells expressing reporter protein B are then screened or selected for those cells which do not express the first reporter protein A, or express reporter protein A only at a low level. These cells harbor the most efficient functional oligonucleotide molecules which then can be identified by characterizing the vectors in the cells.

The vectors can be autonomously replicating vectors, viral vectors, nucleic acids that integrate into the host chromosome, and transiently expressed nucleic acid molecules. The reporter genes can be expressed using any suitable expression sequences. Numerous expression sequences are known and can be used for expression of the reporter genes. Expression sequences can generally be classified as promoters, terminators, and, for use in eukaryotic cells, enhancers. Expression in prokaryotic cells also requires a Shine-Dalgamo sequence just upstream of the coding region for proper translation initiation. Inducible promoters are preferred for use with the first reporter gene since it is preferred that expression of the first reporter gene be adjustable.

It is preferred that plasmid vectors containing promoters and control sequences which are derived from species compatible with the host cell be used with these hosts. It is preferred that the vector carry a replication sequence. The vectors can be used to transiently transfect or transform host cells, or can be integrated into the host cell chromosome. Preferably, however, the vectors include sequences that allow replication of the vector and stable or semi-stable maintenance of the vector in the host cell. Many such sequences for use in various eukaryotic and prokaryotic cells are known and their use in vectors routine. Generally, it is preferred that replication sequences known to function in host cells of interest be used. For example, use of the origin of replication from vectors such as pBR322 and pUC19 are preferred for prokaryotic cells, origins of replication from such vectors as YEP24 and YRP17 are preferred for fungal cells, and origins of replication from SV40 and pEGFP-N are preferred for eukaryotic cells. All of these examples are commercially available (New England Biolabs; Clontech).

A preferred vector for use in prokaryotic cells is Bluescript-SK$^+$ (Stratagene). A preferred vector for use in eukaryotic cells is the shuttle vector pEGFP-N (Clontech). This vector encodes a green fluorescent protein (GFP) that has been optimized for maximal activity in mammalian cells and is designed for expression of GFP fusion proteins. This vector also contains a multiple cloning site (MCS) 5' to the GFP sequence which is designed for creating fusion proteins in all three reading frames. The MCS can be used for inserting DNA encoding an RNA of interest to generate a gene encoding a fusion transcript which encodes a fusion protein.

Reporter proteins can be any proteins which can be detected either directly or indirectly. These include enzymes, such as β-galactosidase, luciferase, and alkaline phosphatase, that can produce specific detectable products, and proteins that can be directly detected. Virtually any protein can be directly detected by using, for example, specific antibodies to the protein. A preferred reporter protein that can be directly detected is the green fluorescent protein (GFP). GFP, from the jellyfish *Aequorea victoria*, produces fluorescence upon exposure to ultraviolet light without the addition of a substrate (Chalfie et al., *Science* 263:802–5 (1994)). A number of modified GFPs have been created that generate as much as 50-fold greater fluorescence than does wild type GFP under standard conditions (Cormack et al., *Gene* 173:33–8 (1996); Zolotukhin et al., *J. Virol* 70:4646–54 (1996)). This level of fluorescence allows the detection of low levels of expression in cells.

Reporter proteins producing a fluorescent signal are useful since such a signal allows cells to be sorted using FACS. Another way of sorting cells based on expression of the reporter protein involves using the reporter protein as a hook to bind cells. For example, a cell surface protein such as a receptor protein can be bound by a specific antibody. Cells expressing such a reporter protein can be captured by, for example, using antibodies bound to a solid substrate, using antibodies bound to magnetic beads, or capturing antibodies bound to the reporter protein. Many techniques for the use of antibodies as capture agents are known and can be used with the disclosed method. A preferred form of cell surface protein for use as the first reporter protein is CD8 when the second reporter protein is CD4, otherwise CD4 is preferred.

The reporter protein can also be a protein that regulates the expression of another gene. This allows detection of expression of the reporter protein by detecting expression of the regulated gene. For example, a repressor protein can be used as the reporter protein. Inhibition of expression of the reporter protein would then result in derepression of the regulated gene. This type of indirect detection allows positive detection of inhibition of the expression of the reporter protein by the functional oligonucleotide molecule. One preferred form of this type of regulation is the use of an antibiotic resistance gene regulated by a repressor protein used as the reporter protein. By exposing the host cells to the antibiotic, only those cells in which expression of the reporter gene has been inhibited will grow since expression of the antibiotic resistance gene will be derepressed. It is preferred that the second reporter protein be a protein that confers antibiotic resistance on the host cell or a cell surface protein. The use of an antibiotic resistance protein is preferred in prokaryotic host cells, and the use of a cell surface protein is preferred in eukaryotic host cells. The most preferred cell surface protein for use as the second reporter protein is CD4.

Genes encoding proteins for use as selection agents can also be inserted into the vectors. Exemplary agents are shown in Table 1. Agents can confer resistance to an antibiotic or other toxic agent to the cell, or aid in selection of cells containing functional oligonucleotide molecules.

TABLE 1

Selection Agents

| AGENT | AGENT FUNCTION |
| --- | --- |
| Cycloserine | analog of D-Ala. Inhibits peptidoglycan synthesis enzymes |
| Glycine | At concentrations greater than 2%, inhibits cell wall biosynthesis enzymes |
| 5 Fluoro 2' Deoxyuridine | Nucleoside analogue inhibits thymidylate synthetase and DNA synthesis |
| 5 Fluoro 5' Deoxyuridine | Nucleoside analogue inhibits thymidylate synthetase and DNA synthesis |
| 5 Fluoroorotic Acid | Toxic nucleic acid analogue |
| Cobalt | uptake controlled by Mg++ transport system. Accumulation is lethal. |
| Ferrous Iron | Uptake controlled by Mg++ transport system. Accumulation is lethal. |
| Nalidixic Acid | DNA gyrase inhibitor |
| Polymyxin B | Binds to lipid A, increasing cell wall permeability |

The vectors can be constructed using well established recombinant DNA techniques (see, for example, Sambrook et al., Molecular Cloning: A Laboratory Manual, second edition, Cold Spring Harbor Laboratory Press, New York (1990)). It is preferred that a base vector be prepared first. Then DNA encoding an RNA molecule of interest can be inserted into this base vector to form a second base vector. A different second base vector can be constructed for each RNA molecule of interest. Finally, libraries of DNA encoding functional oligonucleotide molecules can be inserted into appropriate second base vectors. The same base vector can be easily used with any RNA molecule of interest, and the same second base vector can be used with any appropriate library of functional oligonucleotide molecules. For example, the same second base vector can be used for a library of ribozymes, a library of EGSs, and a library of antisense RNA molecules.

Host cells can be transformed with the disclosed vectors using any suitable means and cultured in conventional nutrient media modified as is appropriate for inducing promoters, selecting transformants or detecting expression. Suitable culture conditions for host cells, such as temperature and pH, are well known. The concentration of plasmid used for cellular transfection is preferably titrated to reduce the possibility of expression in the same cell of multiple vectors encoding different functional oligonucleotide molecules.

Preferred prokaryotic host cells for use in the disclosed method are *E. coli* cells. Preferred eukaryotic host cells for use in the disclosed method are monkey kidney CVI line transformed by SV40 (COS-7, ATCC CRL 1651); human embryonic kidney line (293, Graham et al. J. Gen Virol. 36:59 [1977]); baby hamster kidney cells (BHK, ATCC CCL 10); chinese hamster ovary-cells-DHFR (CHO, Urlaub and Chasin, Proc. Natl. Acad. Sci. (USA) 77:4216, [1980]); mouse sertoli cells (TM4, Mather, Biol. Reprod. 23:243–251 [1980]); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MT 060562, ATCC CCL51); TRI cells (Mather et al., Annals N.Y. Acad. Sci 383:44–68 (1982)); human B cells (Daudi, ATCC CCL 213); human T cells (MOLT-4, ATCC CRL 1582); and human macrophage cells (U-937, ATCC CRL 1593).

II. Method for Identification of Essential or Functional Genes

A method that employs combinatorial libraries of EGSs to identify mRNAs that encode proteins essential for viability or other function in cells, has been developed. The examples demonstrate the method as used in a bacteria such as *E. coli*.

EGSs are short oligoribonucleotides of the general composition $N_{n\geq 7}NACCA$. If such sequences anneal to complementary sequence in a second RNA, the duplex serves as a substrate for RNase P. RNase P is a ubiquitous enzyme whose normal role in cellular metabolism is 5' end maturation of transfer RNA. All characterized RNase P's are comprised of RNA and protein components. In bacteria, there is a single protein subunit and a single RNA subunit; the RNA component is catalytic. In tRNA maturation, RNase P recognizes determinants in the acceptor stem, the D loop and the non-duplexed CCA; indeed the CCA is known to form base pairs with the RNA subunit of the enzyme.

The EGS binds via base pairing to another RNA (the target). The RNA—RNA duplex mimics the natural tRNA substrate of RNase P and recruits the enzyme, which cleaves the target RNA at the single-strand/double-strand boundary. There exist no known sequence or base composition restrictions on the helical region; accordingly EGSs can, in theory, direct RNase P cleavage of any RNA in the cell, including mRNA. The ability of RNase P to cleave RNAs other than its natural substrates serves as the underlying rationale for methodology described below.

General outline of the experimental strategy for identification of mRNAs encoding essential genes The underlying assumption in the experimental design is that all (or most) mRNAs can be cleaved by RNase P in the presence of an appropriate EGS sequence. Thus, if all possible EGS sequences can be expressed, a subset of these will cause cleavage of mRNAs encoding proteins essential for cell viability. Recovery and characterization of these "active" EGS sequences allows identification of the targeted mRNA (gene) via a variety of strategies. Necessary prerequisites for the successful application of this concept include the ability to synthesize and express all or most possible EGSs and a method to isolate the EGSs that elicit the desired phenotype (e.g. cell death). Further there perforce must exist EGSs capable of causing near complete destruction of the message of interest.

In this regard, it is not at present possible to predict which EGSs will be most effective. Using rational design, Altman and colleagues could achieve only modest reduction of specific mRNAs using single EGS sequences (Guerrier-Takeda, C., et al. *Proc. Natl. Acad. USA* 94, 8468–8472, 1997). Biologically significant reduction was observed when EGS sequences were used either in combination (i.e. multiple EGSs targeted to the same mRNA) or when the ratio of EGS/target was extremely high. To ascertain whether it was feasible or reasonable to expect that a single EGS could severely down-regulate the expression of a specific mRNA, a library of fifty-two EGS sequences targeted to the chloramphenicol acetyltransferase mRNA was designed and found that only one of the fifty-two EGS caused $\geq 90\%$ reduction in gene expression. These experiments are summarized in detail below in Example 4. The results of these examples have three important implications to the design of the method to identify essential or functional genes: 1) it is reasonable to expect that a single EGS can elicit complete or near complete degradation of a specific mRNA; 2) only approximately one in fifty EGS sequences is likely to achieve the level of inhibition required; and 3) current methods of predicting those EGSs that are likely to be active in vivo are unreliable. This last consideration makes it highly unlikely that appropriate EGS sequences could be designed to assess in a systematic way the function of each known gene in a bacterial genome. Furthermore, the fact that only a small subset of EGSs targeted to a specific gene are likely to elicit a biological effect impinges on the design of a genome wide screen and the interpretation of results.

Based on calculations as shown in the examples, the random or overlapping sequence in the EGSs for use in identifying essential or functional genes in bacteria will typically be between $N_{10-13}$; in fungi, it will typically be between $N_{10-15}$, and in mammalian cells, it will typically be between $N_{10-18}$, followed by sequence required to target the RNase P of the host cell to cleave the targeted RNA. In the case of the prokaryotic RNase P, this is as simple as ACCA; the structures required for the eukaryotic RNase P are more complex, and can be designed as necessary as discussed above, to create a structure similar to that of a portion of a tRNA molecule.

This method will be further understood by reference to the following non-limiting examples.

EXAMPLE 1

Initial Proof of Principle of Genome Wide Functional Analysis Using Libraries of EGS Sequences Design of EGSs Initial experiments employed 13mer EGS sequences where the two 3' most positions were fixed as cytosines. Accordingly, the EGS had the sequence $N_{11}CC$, followed by ACCA: 5'-$N_{11}$CCACCA-3'. Thirteen was chosen because any specific 13mer should be statistically unique in the *E. coli* genome which has a complexity of approximately $4\times10^6$ base pairs, or $8\times10^6$ if both strands are considered separately. Note that the effective complexity of the genome is $4\times10^6$ because only one strand of DNA is transcribed. The chance of finding any specific 13mer sequence is approximately $\frac{1}{3}\times10^7$. The second consideration involved in choosing 13mer sequences was the fact that 13 was the shortest EGS known at the time of the experiment to elicit an effect in vivo.

Conditional expression of EGS sequences

The overall goal of the experimental design is the identification of EGS sequences that elicit cleavage of mRNAs encoding proteins essential for viability. A straightforward and explicit consequence of this design is that EGS expression must be regulatable; i.e. if EGS expression was constitute, those cells harboring the desired sequence would die and consequently the appropriate cells would be lost upon propagation of the library. There are many regulatable promoters known in *E. coli*. Particularly preferred promoters initiate transcription at the site of insertion of foreign sequences (e.g. the regulatable arabinose promoter). The example uses the ara C-pBAD system for conditional expression of EGS sequences. This is a tightly regulated system where transcription is repressed in the absence of arabinose and induced in the presence of low levels of arabinose.

Figure 2A:
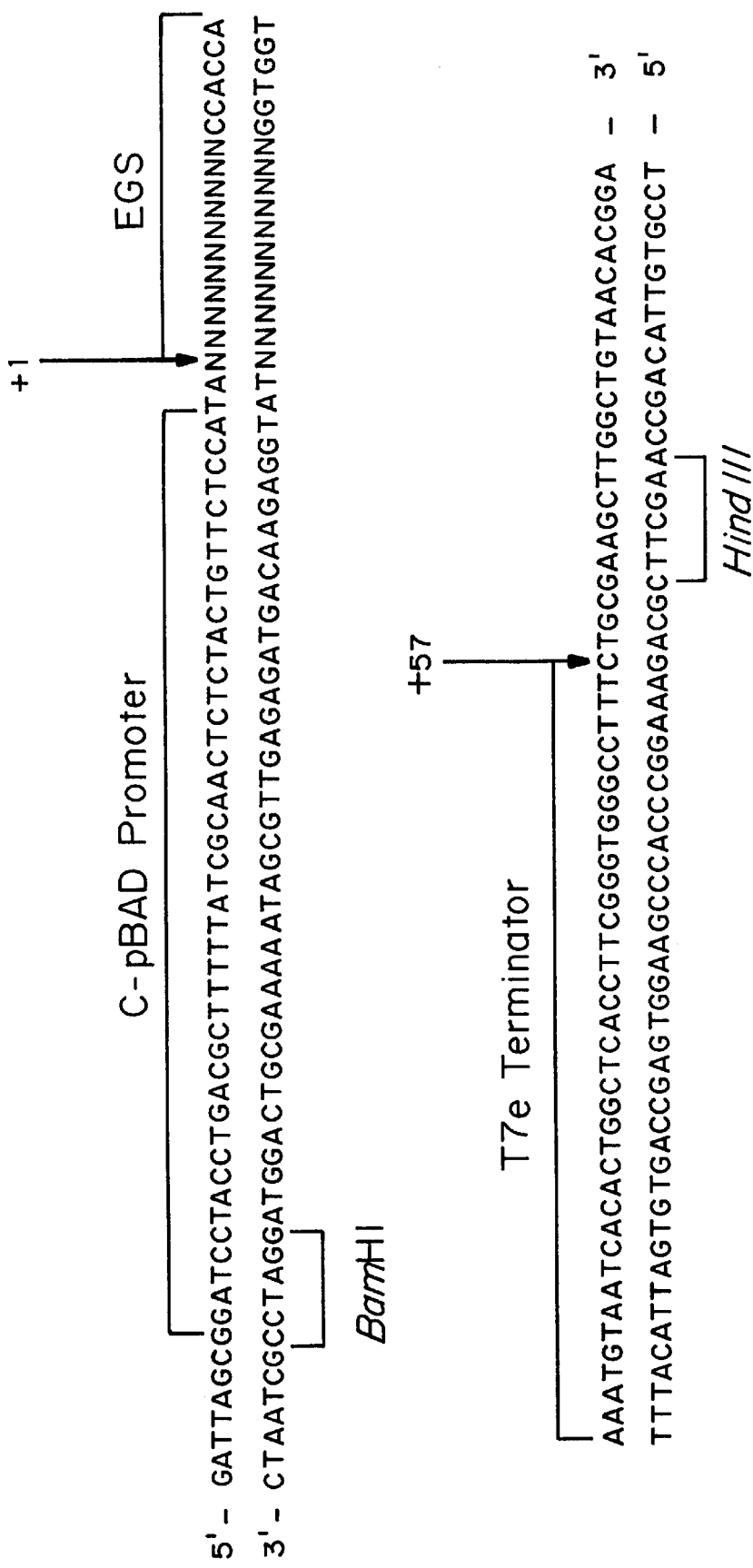
FIG. 2A is a diagram of the constructs used in the examples to make an ARA-N11 library (13-mer EGSs, $N_{11}$CCACCA; SEQ ID NO:3), for use in identifying essential genes in E. coli.
Figure 2B:
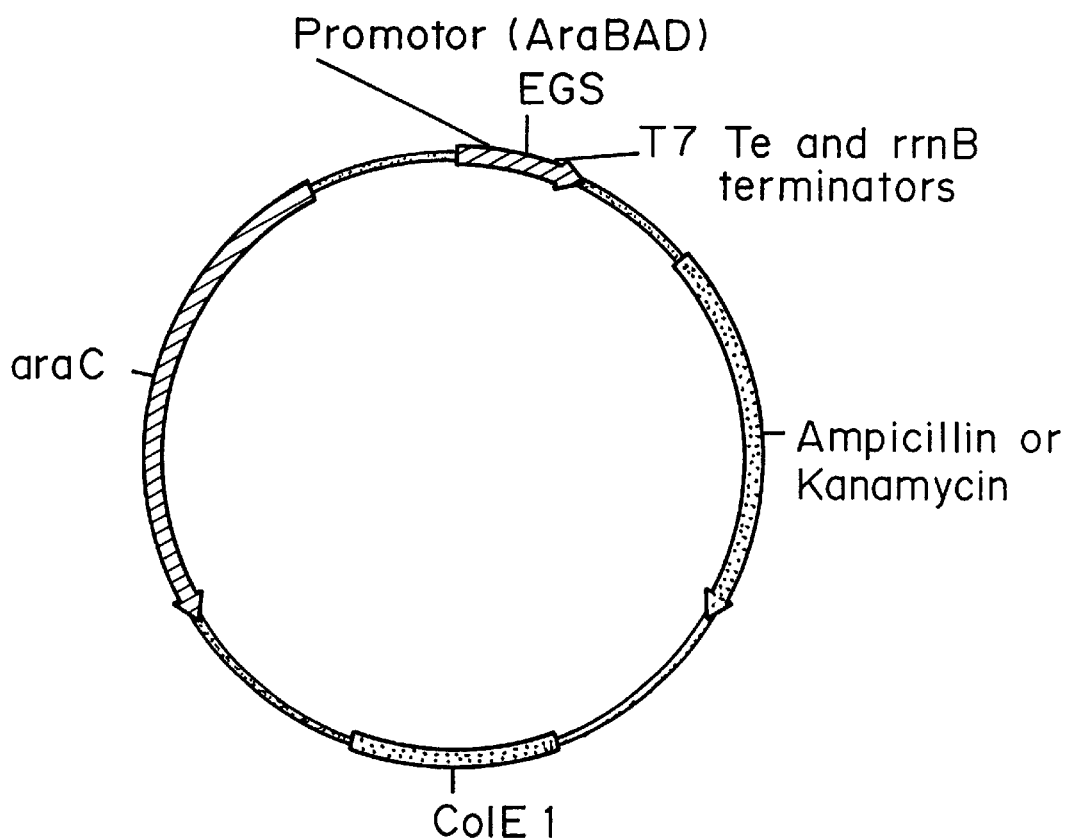
FIG. 2B is a schematic of the pARANx (A/K) EGS transcription vector.
Figure 2C:
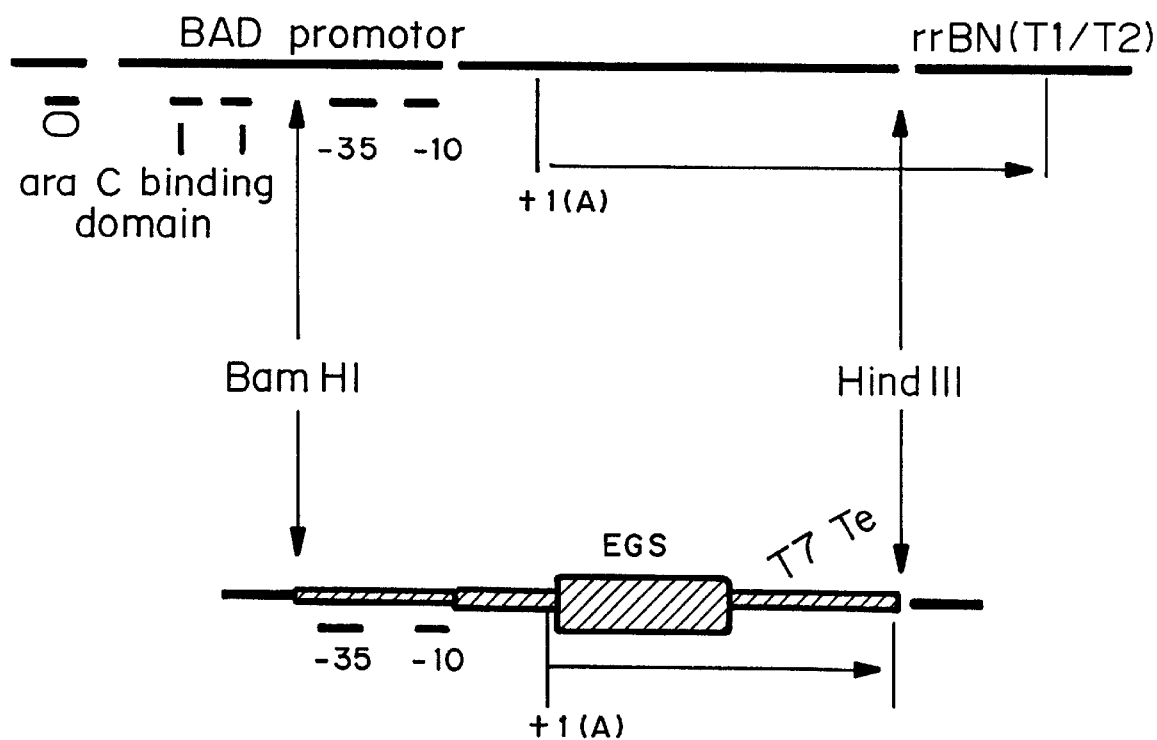
FIG. 2C is a schematic of the pARAN vector and library construction.

FIGS. 2A–C shows the constructs and plasmids used in the experiments. The ara c-pBAD promoter is immediately juxtaposed to an invariant A (to facilitate initiation of transcription) followed by the EGS-ACCA sequence. This sequence in turn is followed by the T7e transcriptional terminator. Transcripts from such constructs contain the EGS-ACCA sequence and the terminator. Altman previously observed that sequence 3' to the EGS-ACCA does not interfere with EGS function. Indeed, the presence of the terminator sequence with its attendant 3' stem loop structure enhances EGS-mediated activity, presumably because the stem-loop renders the short transcripts more resistant to decay. Thus, EGS sequences attached to the terminator accumulate to higher steady state levels than EGS sequence alone (i.e. those generated by cis-acting ribozymes).

The expression was assessed by RNA blot analysis of EGS sequence under a variety of conditions. As expected, no expression is observed in cells harboring the EGS plasmid if arabinose is not added to the growth media. In the presence of arabinose, EGS expression is readily detected and a high steady state level of transcript is observed following 30 minutes of induction. This level of expression is maintained for several hours.

Design of combinatorial EGS libraries

A library of randomized EGSs was created by ligating the appropriate DNA insert into the pBAD plasmid to express all possible EGS sequences. The ligated plasmids were then used to transform $E.\ coli$. Sufficient independent transformants were obtained to insure that the entire library was represented (complexity of EGS sequences was approximately $4 \times 10^6$; independent transformants obtained was approximately $2 \times 10^7$; this number of transformants gives 95% confidence that all members of the library are represented). Following transformation, the library (each bacteria contains one plasmid, hence one EGS) was amplified via liquid growth under non-inducing conditions. Many (greater than 50) individual plasmids, were then purified and sequenced to verify that the sequence of the insert was correct and that there were no nucleotide biases in the randomized (EGS) region.

Initial tests of efficacy of the 13mer EGS library.

The identification of those EGS sequences that, when expressed, cause lethality, normally involves the analysis of many thousands of individual bacterial colonies. Accordingly, a technique was developed to prove the utility of the EGS libraries via a streamlined approach. The method takes advantage of the fact that several chemical agents are toxic to $E.\ coli$ only when certain non-essential genes are expressed. Thus, survival of bacteria in the presence of such agents is dependent upon the absence of a functional gene product. For example, high levels of cobalt are lethal to $E.\ coli$. This lethality results from accumulation of cobalt ion inside the cell. If cobalt is prevented from entering the cell (i.e. by inactivation of an ion-transporter) the cells survive. Several such toxic agents were selected (Table 1) and studies undertaken to recover cells that survived the toxic treatment if and only if an appropriate EGS was expressed.

Figure 3:
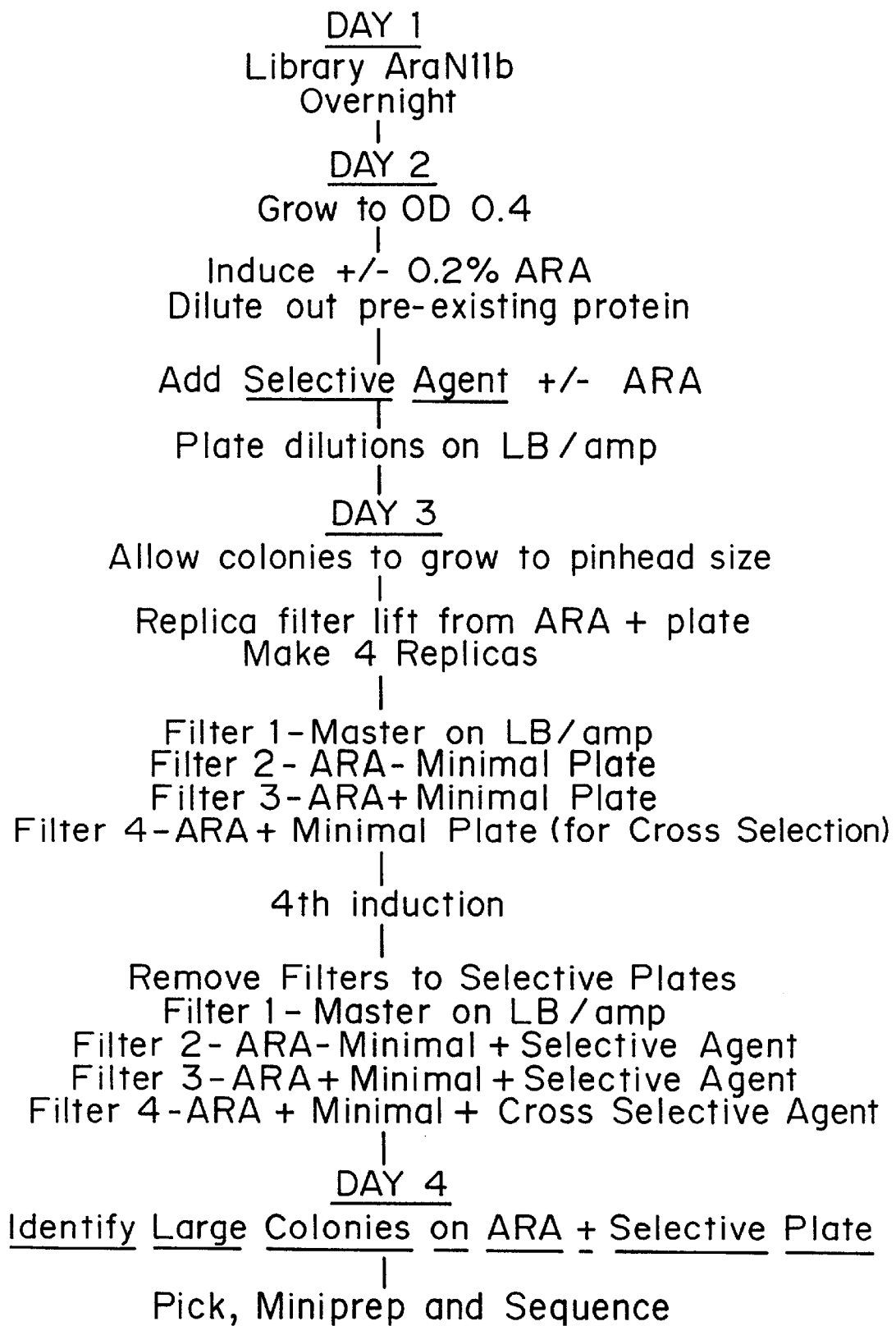
FIG. 3 is a flow diagram of the method for induction and selection on solid media of the AraN11 library in E. coli. Only cells expressing an appropriate EGS survive and are amplified.

Colonies were then screened for arabinose (inducer)-specific survival. Non-arabinose inducer dependent survivors could arise by spontaneous mutation of the relevant gene(s). An outline of the experimental design is shown in FIG. 3. Briefly, cells were allowed to grow to log phase and then were exposed to arabinose. At this point, EGS expression was induced. The cells were then left in arabinose for several generations prior to treatment with the toxic agent. This incubation time is important because the EGS only affects mRNA levels and does not influence pre-existing proteins. Thus, the pre-existing protein must decay (or be diluted via growth) prior to selection.

Following appropriate incubation, populations of cells were treated individually with selective agents and survivors were recovered. After removal of the selective agent, cells were plated on non-selective media such that individual colonies could be analyzed. At this point individual clones were then assayed for their ability to survive the selective treatment in the presence or absence of arabinose. Importantly, for each of seven different selective agents, several arabinose-dependent (i.e. EGS-dependent) survivors were recovered. Equally important, the resistance phenotypes observed were highly specific; i.e. those EGSs that conferred resistance to one selective agent did not confer resistance to any other of the agents. Finally, unambiguous evidence linking the resistance phenotype to a specific EGS was obtained by retransformation of naive bacteria with plasmids expressing the appropriate EGS sequence.

The nucleotide sequence of each active clone was then determined and compared with the published nucleotide sequence of $E.\ coli$. It was anticipated that the active EGS sequences would be complementary to transcribed regions of the genome. However, in no case was perfect complementarity (Watson-Crick) observed. These observations indicated that, among other possibilities, thirteen nucleotides of EGS sequence may contain informational content in excess of that required for biological function. These experiments with selective agents demonstrated unequivocally that:

1. High penetrance, high specificity, conditional phenotypes are elicited by EGS sequences
2. Active EGS sequences can be efficiently and rapidly isolated from complex libraries.

EXAMPLE 2

Isolation and Characterization of EGS Sequences that when Expressed Cause Impairment of Growth or Lethality The experiments described in Example 1 demonstrated EGS-dependent survival in the presence of certain selective agents. To prove more directly the utility of the EGS-mediated approach for identification of essential genes, studies were conducted to obtain EGS sequences that, when expressed, caused a loss of viability. Although similar, these experiments differ somewhat in design from those outlined in Example 1, i.e. there is no way to select for dead or dying cells. Accordingly, it is necessary to screen for those EGSs whose expression leads to impairment of growth.

The most straightforward way to screen for a lethal phenotype is by "replica plating". In such an approach, individual clones (colonies arising from a single bacterium) are arrayed in any of a variety of ways, and replicate arrays are generated. In its simplest form, comparing the growth of colonies either in the presence or absence of inducer (and hence EGS) reveals those EGSs that cause a growth defect. Confirmation that the defect is EGS-mediated can be done in a variety of ways, including retransformation.

The praticality of screening for lethal EGS sequences using simple replica plating depends upon the complexity of the library and the frequency of expected positives. Using the limited available data, it is possible to estimate the expected number of "positive" clones. The $E.\ coli$ genome has a complexity of $4.6 \times 10^6$ bp. If one assumes a transcription density approaching 100% and little, if any, symmetric transcription, the transcribed complexity is also $4.6 \times 10^6$. Further, a reasonable estimate of essential genes is approximately 10%. Assuming that there is not a significant disparity in average size between essential and non-essential genes, the effective target size for EGSs eliciting a lethal phenotype would be $4.6 \times 10^5$ bases or about 400 genes of 1 kb (not taking into consideration polarity effects and the fact that a majority of genes in $E.\ coli$ are transcribed as part of operons). From the data set obtained with the second method as shown by Example 4, it is likely that only about 2% of the targetable nucleotides are "accessible", or approximately 10,000 targets distributed throughout the genome. Thus, with a truly randomized library, one would expect approximately 10,000 active EGSs. In the case of the $N_{11}CC$ library only 1/16 of the possible sites would be targetable, reducing the number of active EGSs to several hundred. Given these considerations (and acknowledging the assumptions) the $N_{11}CC$ library, which has a complexity of $4 \times 10^6$, would yield one positive clone per 10,000 clones examined.

Figure 4:
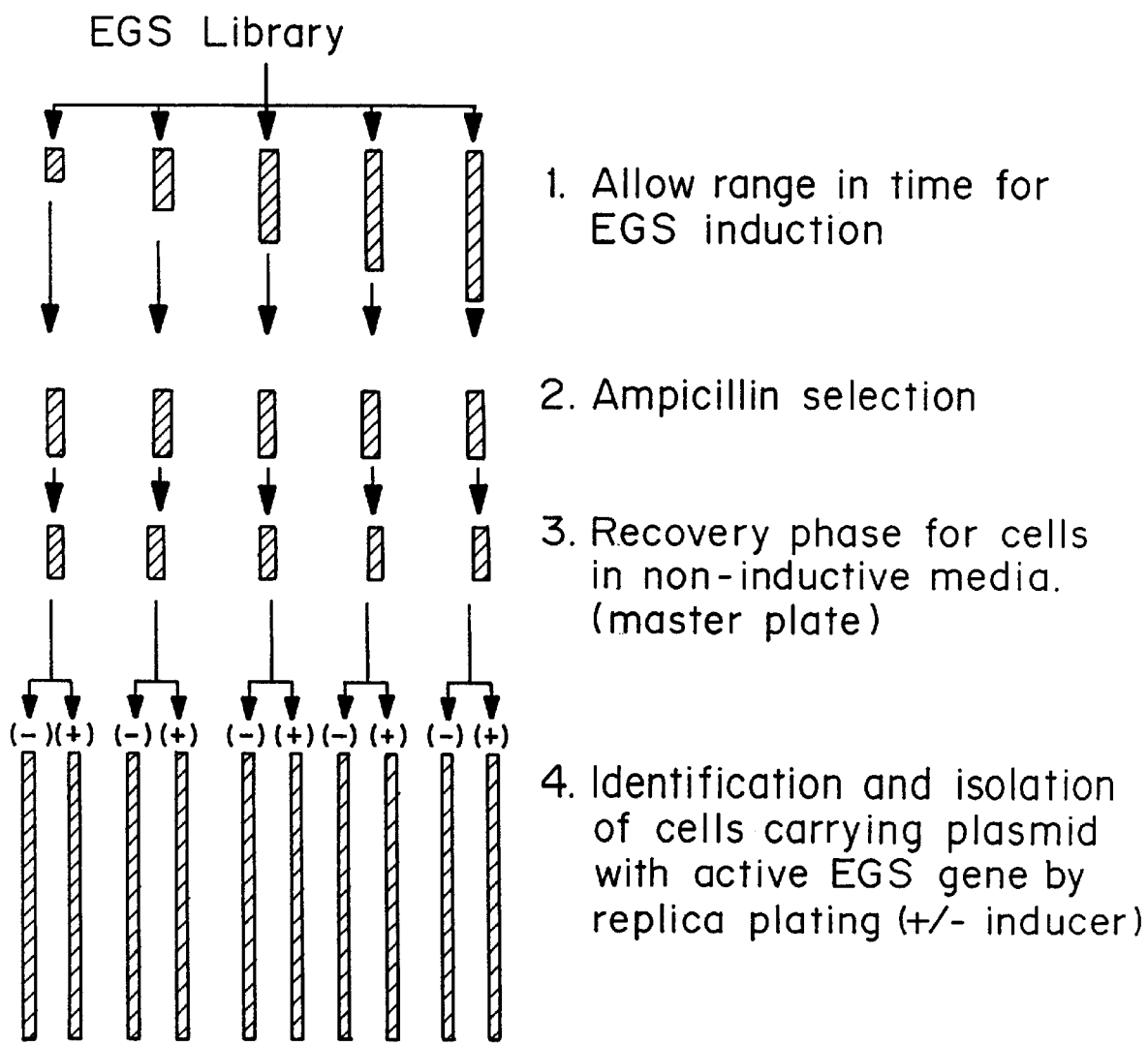
FIG. 4 is a flow diagram of the ampicillin enrichment method for selection of EGS targeting essential genes.
Figure 5A:
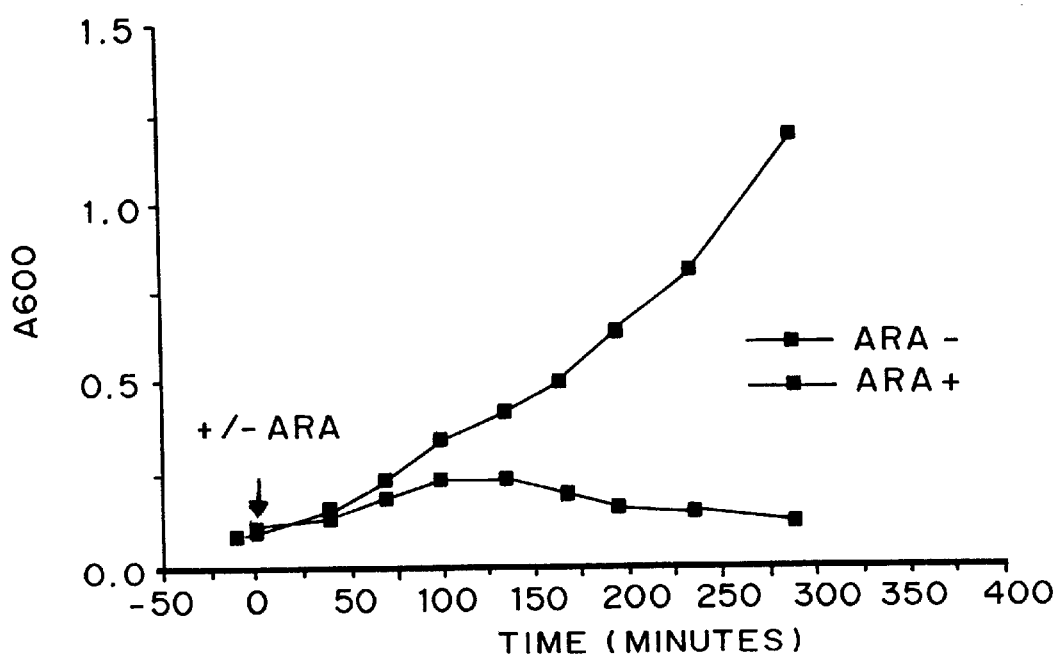
FIGS. 5A and 5B are graphs of the growth of ampicillin selected clone E8-1 (FIG. 5A) and growth of control (FIG. 5B) with (circles) and without (squares) arabinose.
Figure 5B:
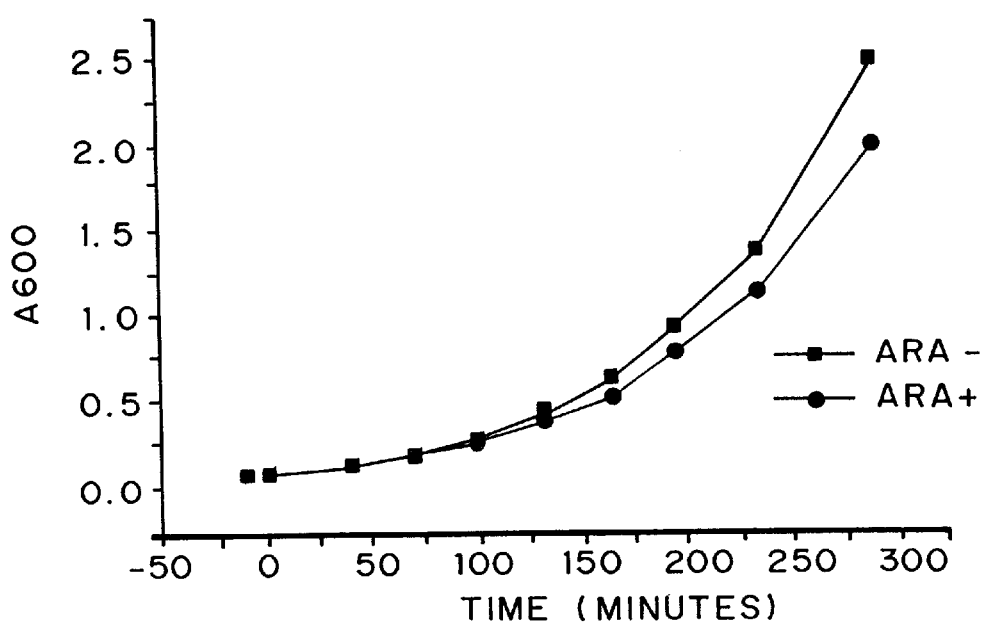
Figure 6:
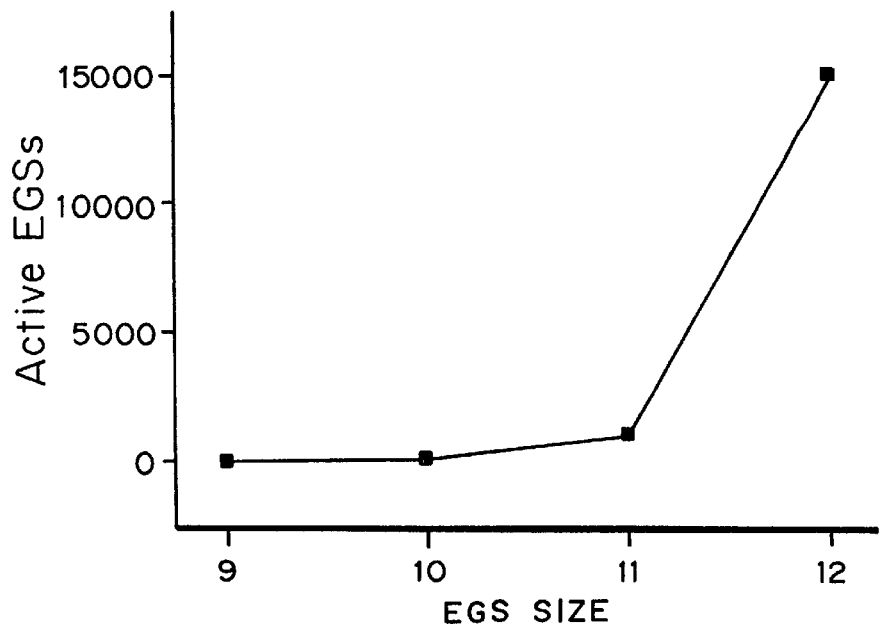
FIG. 6 is a graph of the relative numbers of active EGSs identified in libraries of different size EGSs: 9-mers, 10-mers, 11-mers, and 12-mers.
Figure 7:
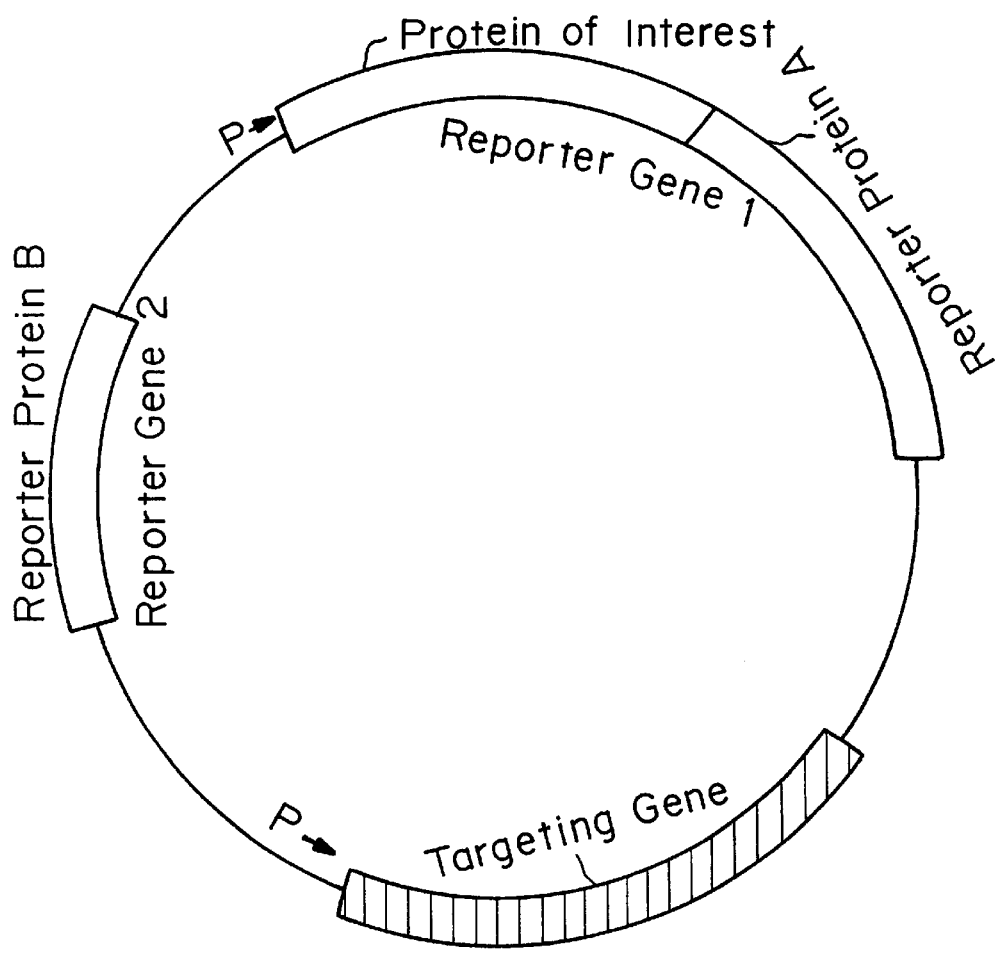
FIG. 7 is a diagram of an example of a vector for use in the method for identifying functional oligonucleotide molecules including EGS, ribozymes, and antisense. Reporter gene 1 encodes a fusion transcript made up of an RNA of interest and RNA encoding a reporter protein (reporter protein A). The fusion transcript encodes a fusion protein made up of the protein encoded by the RNA of interest and reporter protein A. Reporter gene 2 encodes reporter protein B. The targeting gene encodes one of the functional oligonucleotide molecules to be tested.
Figure 8:
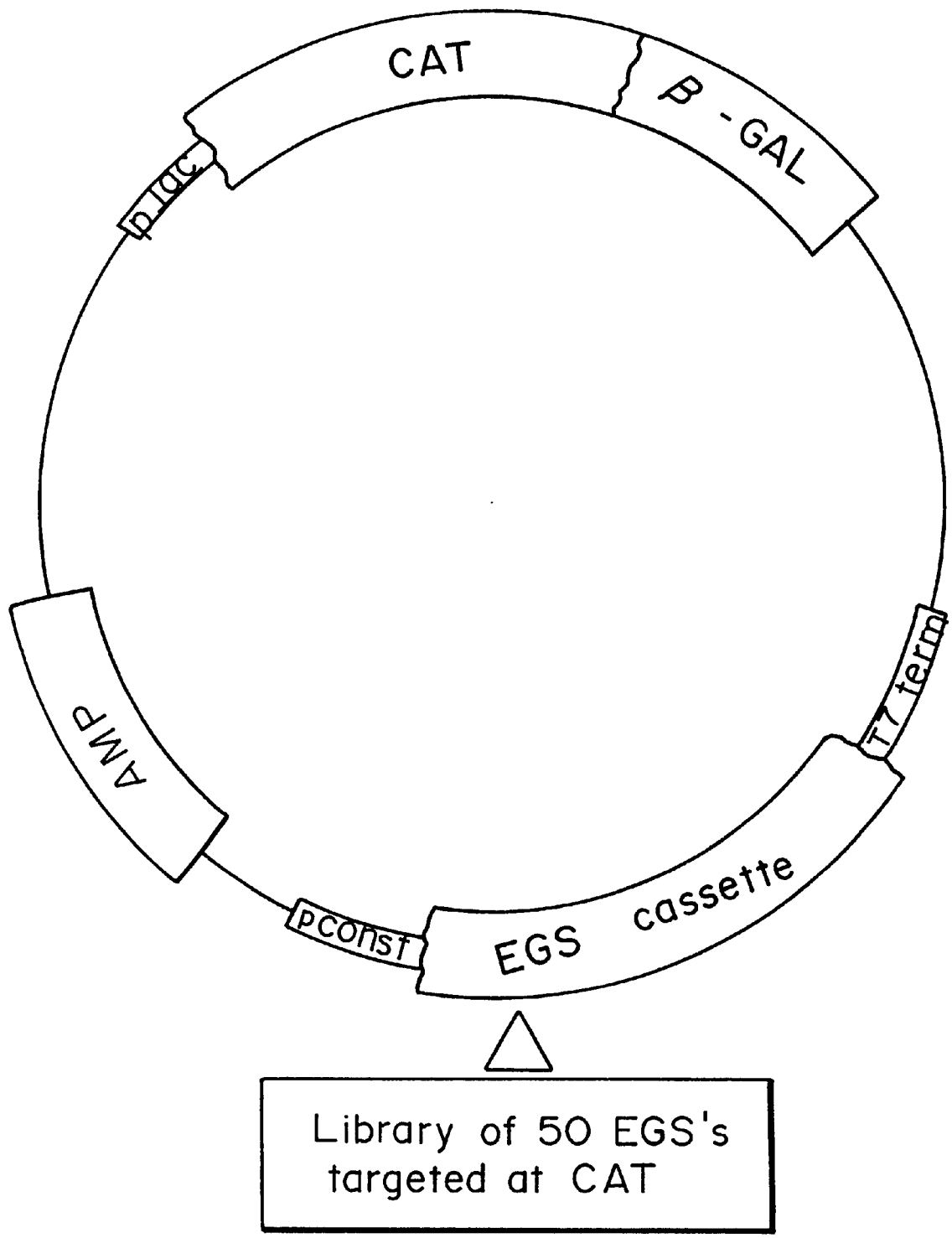
FIG. 8 is a diagram of an example of a vector for use in the method to identify functional oligonucleotide molecules. Reporter gene 1 encodes a fusion transcript made up of an RNA encoding chloramphenicol acetyltransferase (CAT) and RNA encoding β-galactosidase (reporter protein A). The fusion transcript encodes a fusion protein made up of CAT and β-galactosidase. Reporter gene 2 is an ampicillin resistance gene. The targeting gene is an EGS cassette encoding one of a library of 50 EGS molecules, each targeted to a different site in the CAT RNA.

One in $10^4$ is an unacceptably low number to contemplate assaying by direct replica plating, so the frequency of active clones was increased using the classical techniques of penicillin enrichment. Penicillin enrichment has been used for decades in microbiological research to aid in the recovery of rare mutations. The technique is based upon the fact that penicillin, or its various derivatives including ampicillin, kill only actively growing cells; cells that are not growing escape penicillin killing. The application of this enrichment strategy to isolation of lethal EGSs is fairly straightforward. Briefly, after induction of EGS expression with arabinose, those cells harboring "effective" EGSs (i.e. those targeted to essential genes) will cease to grow and thus become resistant to penicillin killing. Importantly, the time at which individual cells cease growing is a function of how long it takes (via turnover or dilution) for the preexisting protein of interest to decline below a viable threshold of activity. Accordingly, to enrich for lethal EGSs targeted to mRNAs encoding different essential proteins it is necessary to treat with penicillin at various times post induction (see FIG. 4).

An enrichment experiment was performed as outlined above and, following amplification of survivors, cells recovered at various times post induction were assayed for inducer dependent lethality via replica plating. Several clones were recovered that demonstrated unambiguous growth defects only in the presence of inducer. As described above, the relevant plasmids were recovered, sequenced, and retransformed into naive bacteria. In every case, the phenotype (slow or no growth) was shown to be due to the presence and expression of the specific EGS sequence. As with the EGSs recovered from the selections described above, the nucleotide sequences were compared with the *E. coli* genomic sequence. Again, there was not perfect (Watson-Crick) complementarity between the recovered EGSs and the published sequences.

These experiments demonstrate directly that it is possible to isolate specific EGS sequences that when expressed, elicit a clear growth-defective phenotype in *E. coli*. Further, they demonstrate the utility of using penicillin treatment to enrich for active EGS sequences. In summary the experiments described above show that:

1. Libraries of EGS sequences can be constructed and expressed under tight regulation and
2. These complex libraries can be "sorted" such that specific EGSs conferring a variety of phenotypes, including lethality can be recovered and characterized.

EXAMPLE 3
Analysis of EGS Libraries in Which the Targeting (Guide) Sequence is Less than Thirteen Nucleotides
Rationale As discussed in Example 2, specific EGSs comprised of a thirteen base guide sequence plus ACCA were shown to elicit high pentrance phenotypes in *E. coli*. However, using conventional (Watson-Crick) base-pairing rules, it was not possible to find perfect complementarity between the EGS sequence and the *E. coli* genomic sequence. These results could be interpreted in a variety of ways including:

1. The thirteen mers provided "excess" information. In such a case, some degree of mismatch between the EGS and target would be allowed. However, there is no a priori way to distinguish which position might be mismatched.
2. The most "efficient" EGSs were selected based upon non Watson-Crick interactions with the target. Such interactions might include wobble pairing or specific tertiary structures. Again, it would not be possible to predict or exclude these types of interactions without prior knowledge of the target.

Given the uncertainty involved in linking the EGS sequence to a specific target, it was essential to systematically investigate the minimal length requirements for EGS activity in vivo. Further, it was desirable to determine the absolute activity of each specific library; i.e. in the absence of selection or enrichment. The assay chosen for activity was the inducible-lethal (growth defect) phenotype described in Example 2. These experiments were carried out in complete media to avoid collecting inducible (EGS dependent) auxotrophs (a significant fraction of the *E. coli* genome becomes essential in minimal media). Four libraries of EGS sequences where the length of the guide was incrementally varied from nine to twelve; i.e. $N_9ACCA$, $N_{10}ACCA$, $N_{11}AACCA$ and $N_{12}ACCA$ were prepared to explore the length requirement in vivo. Unlike the 13mer library described above, no bases in the guide sequence were held invariant. In all cases, sufficient transformants (5×complexity) were obtained to insure adequate representation.

Analysis of the $N_9ACCA$ and $N_{10}ACCA$ libraries.

To assess the activity of the $N_9$ and $N_{10}$ libraries, approximately 45,000 individual clones from each were assayed for their ability to form colonies in the presence or absence of EGS expression, i.e. in the presence or absence of arabinose. The complexity of the $N_9$ library is approximately $2.6 \times 10^5$; and the complexity of the $N_{10}$ library is approximately $1 \times 10^6$. With both libraries, very few positive clones were found. The extrapolated number of "active" molecules in the $N_9$ library was $\geq 50$ and the extrapolated number of "active" molecules in the $N_{10}$ library was approximately 100. Further analysis of the $N_9$ library, via penicillin enrichment to facilitate recovery of active clones, revealed that most of the clones that elicited a phenotype could be aligned as part of a simple nucleotide sequence. The 10mer library was not analyzed further.

The fact that both 9 and 10mer libraries were essentially inert is important because these results define a lower boundary on the length of biologically active EGS sequences in vivo. Further, these results are significant when juxtaposed with the findings with the 13mer library. Clearly, the 13mers contain within them all possible 9 and 10mers, yet one was able with the 13mer library to recover multiple distinct clones conferring a variety of phenotypes. A reasonable interpretation of the two sets of results is that the 13mers could tolerate at most two mismatches while retaining activity. Finally, and not unimportantly, the results with the short EGS sequences indicates that the minimum length of a biologically active EGS in *E. coli* is approximately the length of sequence necessary to be statistically unique in the bacterial genome.

Analysis of the $N_{11}ACCA$ library

The absolute, unenriched activity of the 11mer library was determined by the analysis of 45,000 independent colonies. Extrapolating from the number of active (growth-inhibitory) EGS sequences in this population, the 11mer library contains between approximately 1,200 and 1,400 active molecules, out of a total complexity of approximately $4 \times 10^6$. The increase in activity in the 11mer library relative to the 9 and 10mer libraries suggested that a total complementarity of 11 was the minimum to elicit significant biological activity. Furthermore, the number of "active" EGS sequences was in excess of the predicted total number of "essential" genes, but considerably below a conservative estimate of the number of total active EGSs predicted by the second method exemplified by Example 4. Because of these considerations, a significant number (greater than 50) of active 11mers was analyzed via nucleotide sequence determination. Many, but not all, of these sequences had perfect (Watson-Crick) complementarity to transcribed regions of the E. coli genome. Several of those with such complementarity were predicted to inactivate mRNAs known to encode proteins essential for viability in E. coli, others identified mRNAs of unknown function (Table 2).

TABLE 2

N11 ACTIVE EGS (SEQ ID NO:4 to SEQ ID NO:38)

| | | |
|---|---|---|
| TACGACGCGAC | CGCACGCGATG | TACAACTGCCC |
| GCTTCGAAGAC | TGGCGCGACGA | ATCTCAGAACC |
| CGCGATGACTC | GTGATGCGGCG | GTGTCTGTTGC |
| CTAGTGACGCG | TGTTTGGCGAT | GCGATAGCTAA |
| AGATGACGTGG | CAGCCATTCAA | GCGACCGTGGC |
| CCGACGACAGC | CCGACGACAGC | CCATAATATCT |
| GTGTGTAAGCG | TCCTGGAGAAG | CATCCTCTTAC |
| CTATCCAACAG | CGTAAGCGACG | GACGTGACGAA |
| CCGAATAGTGT | GACGACGAGGC | CAGCTTTTGC* |
| TGCCAACTTAC | GTAGAGCGACG | CACGACGAGGC |
| TCAGCCAATGC | GGATGTGAGCC | GAAGCGTTCAG |
| CATTTAACAAC | TGATAGTTTCC | |

It is not yet known whether the complementaries observed are biologically relevant; however, at least two considerations suggest that 11mers are suboptimal for genomic screening. First, the number of active clones is low. Second, the nucleotide sequence analysis revealed that the active 11mers had amongst themselves pronounced sequence bias. In this regard, out of fifty EGSs sequenced, more than 20 shared a common hexanucleotide, and there were numerous examples of shared hepta and octanucleotides. The linear sequence complexity of 50 11mers is 550 nucleotides. The odds of finding a specific hexanucleotide appearing are 1/4096 and the odds of finding specific longer oligomers correspondingly lower. One possible explanation for these results is that, at short EGS length, RNase P has strong sequence preferences. If true, 11mers might have unacceptably tight target site restrictions. As shown below, both of these limitations (low activity and target site restriction) are not observed with 12mers.

Analysis of $N_{12}ACAA$ libraries

Approximately 50,000 independent clones were assessed for EGS-dependent activity in the 12mer library as described above. There was a dramatic increase in active clones relative to the 11mer library. Approximately 13,000 active molecules were estimated with the 12mer library. This number of active clones is significant because it is well in excess of the number of predicted essential genes and in good agreement with the estimated level of activity predicted by the second method. The nucleotide sequence of fourteen active 12mers is shown in Table 3.

TABLE 3

N12 ACTIVE EGSs (SEQ ID NO:39 to SEQ ID NO:52)

| | |
|---|---|
| CATAACATCCT | CTAACAGCCATT |
| CTGGCTTATCCC | CAGCCACTGCCT |
| ACAACTGCCAATT | CCAGCATGTATC |
| GCGATAGACCAA | CAACTGCCCAAC |
| CAATGACGCGAA | GCTTAGCTCGTA |
| CGGCGATGCGGT | GCCTAACCGGCG |
| CGCGACGGATGG | AGCAGAGCACAG |

Most significantly six of these sequences bind with perfect Watson-Crick base pairing with the target sequence. Some of these targets have been independently confirmed to be essential genes by other techniques.

Importantly these sequences do not display any of the non random character of the 11mers. However, the "active" 12mers characterized to date do not display a statistically significant over representation of unique 12mers present in the transcribed region of the E. coli genome. These results indicate that optimal EGS activity in vivo is not obligatorily linked to conventional (Watson-Crick) base pairing with the target sequence. A corollary of these results is that simple (i.e., straightforward homology matching) computer based searching is unlikely to be definitive in relating active EGSs to their biological target.

Strategies for deconvolution, i.e., unambiguous linkage between active EGS sequences and their target.

As discussed above, the genomes of twelve bacteria (Aquifex aeolocus, Bacillus subtilis, Borrelia burgdorferi, Chlamydia trachomatic, Escherichia coli K-12 MG 1655, Haemophilus influenzae Rd, Helicobacter pylori 16695, Mycobacterium tuberculosis, Mycoplasma genitalium G37, Mycoplasma pneumoniae M129, Rickettsia prowazeidi, Treponema pallidum) are completely sequenced and another thirty-eight (Aquifex aeolicus, Arcanobacterium pyogenes, Bacillus pumilus, Bacillus subtilis, Borrelia burgdorferi, Buchnera aphidicola, Chlamydia trachomatis, Clostridium MCF-1, Corynebacterium glutamicum, Enterobacter aerogenes, Escherichia coli, Haemophilus influenzae, Helicobacter pylori, Lactobacillus delbrueckii, Lactobacillus helveticus subsp. jugurti, Lactobacillus reuteri, Lactococcus lactis, Mycobacterium tuberculosis, Mycoplasma genitalium, Mycoplasma pneumoniae, Pantoea citrea, Pasteurella multocida, Prevotella ruminicola, Rhizobium sp. NGR234, Rhodothermus marinus, Rickettsia prowazekii, Ruminococcus flavefaciens, Salmonella berta, Salmonella typhimurium, Staphylococcus aureus, Streptococcus agalactiae, Streptomyces clavuligerus, Streptomyces nigrifaciens, Streptomyces phaeochromogenes, Synechocystis PCC6803, Treponema pallidum, Yersinia pestis, Zymomonas mobilis) are underway. In the simplest embodiment, the EGSs causing cleavage of an RNA encoding an essential or functional gene is identified by comparison with the known sequence, looking for regions of complementarity by Watson-Crick base pairing.

The examples indicate that not every "active" EGS will match via homology searches a unique transcribed region of a bacterial genome, although a substantial number (for example, six of the fourteen recited in Table 3) may do so. However, this result does not preclude or even suggest that EGS activity is not mediated by base-paring. It seems likely that some, although probably quite limited "wobble" pairing, i.e. G:U, is allowed in the EGS-target duplex. If accurate, it complicates but does not preclude straightforward computer based deconvolution. It is expected that active EGSs will reveal regions of mRNAs that are accessible for hybridization. It is unlikely that these regions will be restricted to a single nucleotide. Therefore, if enough EGSs are analyzed, clusters of overlapping but not identical active clones should be observed. Analysis of these clusters should reveal the actual target of the EGSs and simultaneously, by comparing active EGSs with themselves, reveal whether wobble pairing is permitted.

Although computer-based deconvolution is desirable, it will not prove linkage between the EGS and suspected target. At least two strategies can be be used to provide definitive evidence for EGS mediated inactivation of specific targets. The first is a "genetic" test. Assume that an EGS of interest is thought to target (base-pair with) an mRNA in the coding region. It is possible by taking advantage of degeneracy in the genetic code to alter the nucleotide sequence of an mRNA while retaining its ability to encode the same protein. Ectopic (i.e. plasmid based) expression of the altered mRNA should be immune from EGS attack and thereby rescue the EGS-dependent phenotype. A second approach relies on a direct analysis of expression pattern of RNAs in EGS-expressing cells. The availability of entire genomic sequences has permitted the creation of ordered arrays of the DNA sequence. Such arrays can be created on traditional membranes or on miniaturized micro-chips. If total RNA from a cell population is used to probe such arrays, it is possible to obtain an expression profile of all genes simultaneously. In an EGS-expressing cell, a specific mRNA will be cleaved and correspondingly its expression should be lowered in an array hybridization. This deficit in hybridization reveals the targeted sequences. As cells die or slow their growth, expression of a number of genes will change. This does not present a problem for the application of expression-profiling in EGS target identification because the EGS-mediated effect only becomes apparent after dilution of pre-existing proteins. This phenotypic lag allows an unambiguous determination of the effected-mRNA.

Other applications of EGS-mediated targeting.

The recovered effective EGS-sequences are themselves valuable reagents for attenuating the expression of specific genes. Thus by inducing the expression of specific EGSs it is possible to determine how cells die via a variety of phenotypic analyses. These EGS sequences could be administered exogenously to bacterial populations. Using appropriate delivery vehicles, the EGSs themselves could be used as antibacterial therapeutics.

II. Methods for Identification of Optimal Functional Oligonucleotide Molecules

Vectors and a method for the identification of functional oligonucleotide molecules, such as ribozymes, EGSs, and anti-sense RNA, that inhibit expression of target RNA molecules, are disclosed. The method identifies functional oligonucleotide molecules by selecting for those RNA molecules that alter expression of a fusion transcript, which includes the sequence of an RNA molecule of interest, from a library of potential functional oligonucleotide molecules. Inhibition of expression of the fusion transcript prevents expression of the reporter protein. This allows inhibition of expression to be monitored by detecting expression of the reporter protein, directly or indirectly. Alternatively, expression can be increased relative to expression of the molecules in cells not including the optimal functional oligonucleotide molecule. The inhibition is accomplished by interaction of a nucleic acid molecule involved in the expression of the RNA molecule of interest with a functional oligonucleotide molecule. Ribozymes and EGSs result in cleavage of the fusion transcript, and antisense RNA blocks expression through hybridization to a nucleic acid molecule involved in the expression of the fusion transcript.

Vectors for use in functional oligonucleotide molecule assays include a first reporter gene, a second reporter gene, and a targeting gene. Reporter gene 1 encodes an RNA molecule including an RNA molecule of interest and sequence encoding reporter protein A. The fusion transcript includes in the 5' portion of the transcript, sequence of an RNA molecule of interest and, in the 3' region of the transcript, sequence encoding the first reporter protein. The sequences are joined so that the fusion transcript encodes a fusion protein that is a fusion between the protein encoded by the sequence of the RNA molecule of interest and the reporter protein. This arrangement makes expression of the reporter protein dependent on expression of the RNA of interest. Reporter gene 1 also includes expression sequences necessary for expression of the gene in appropriate host cells. Reporter gene 2 encodes a different reporter protein B. The vector also encodes a functional oligonucleotide molecule either specifically targeted to the RNA of interest or including a degenerate or partially degenerate targeting sequence.

Expression, or lack of expression, of reporter protein A is used to assess the effect of the functional oligonucleotide molecule. Expression of reporter protein B can be used both to detect transformation or transfection of the vector into cells and as a control for effects on the expression of reporter protein A that are not due to cleavage of the RNA molecule of interest.

Although it is preferred that the three components: the first reporter gene, the second reporter gene, and the targeting gene, be included on a single nucleic acid molecule, the reporter genes and the targeting gene may be on separate molecules. When the reporter genes and the targeting gene are on separate molecules, it is preferred that the molecule containing the reporter genes is integrated into the host chromosome. This allows a cell strain containing appropriate reporter genes to be easily maintained and different sets of vectors encoding different libraries of functional oligonucleotide molecules to be conveniently tested against the same reporter gene.

Cells expressing the reporter gene 2 are identified by detecting the presence of reporter protein B either directly or indirectly. Reporter gene 2 is used to insure that the cells contain the vector and to control for any factors that could affect expression in general. Without such a control, a loss of expression of reporter gene 1 could be misinterpreted. It is not important that the level of expression of reporter gene 2 be measured. It is preferred that reporter protein B is an essential protein for the cell, such as a protein that confers antibiotic resistance or a protein that produces a required nutrient not present in culture medium, to facilitate selection.

Cells in which expression of the first reporter gene is altered can be identified by measuring the level of expression of reporter protein A either directly or indirectly, or by separating cells based on the expression level of reporter protein A. The preferred method of detection will depend on the nature of reporter protein being used. For example, when using a reporter protein that produces a detectable signal proportionate to the level of expression, cells can be sorted or picked based on the level of signal produced. Reporter proteins such as β-galactosidase and green fluorescent protein are in this category. When using a cell surface protein as reporter protein A, the cell sorting techniques described above can be used. Cells can also be sorted by FACS when using green fluorescent protein as reporter protein A since it produces a fluorescent signal.

It is preferred that the above selection process can be repeated several times, by isolating vectors from the selected cells and re-introducing them into new cells, until cells bearing a homogeneous population of plasmids can be isolated. Following the final sorting of cells, the vectors can be isolated as described below, amplified, and the sequence of the functional oligonucleotide molecule encoded in each preparation of vector can be determined.

Identification of Functional Ribozymes or EGSs

Functional oligonucleotide molecules that are effective inhibitors of expression of reporter gene 1 can be identified using any suitable technique. It is preferred that the sequence of the functional oligonucleotide molecules be determined by sequencing the vectors in the selected cells. Many techniques for sequencing vector sequences from clones are known and can be used in the disclosed method. For example, Hirt supernatants of selected cells can be made and plasmids will be extracted from those cells. A preferred method for identifying the sequence of the functional oligonucleotide molecules in the isolated vectors is a single cell PCR amplification of the functional nucleotide region, followed by sequencing. Another preferred method for identifying the sequence of the functional oligonucleotide molecules in the isolated vectors is to lyse the cells, extract the plasmids, amplify the plasmids in bacteria, and sequence the amplified plasmids to identify the functional oligonucleotide molecule sequence associated with the cell population.

Functional oligonucleotide molecules identified using the disclosed method can be used to design oligomers argeted to the same site as the functional oligonucleotide molecule.

Transformation in a Single Plasmid

A set of the vectors encoding a first reporter gene encoding GFP as reporter protein A, a second reporter gene, and targeting gene encoding a library of EGS or ribozyme molecules as the functional oligonucleotide molecules are amplified by growing the mixed population in *E. coli*. A fixed concentration of plasmids is complexed with an appropriate carrier (for example, lipid, calcium phosphate, DEAE dextran) and delivered to mammalian cells. At the peak day of expression (usually day two), the level of expression of GFP and the second reporter are measured by FACS sorting. The expression of the second reporter (for example, CD4) is measured at a wavelength that does not overlap with GFP fluorescence spectrum. Typically, an antibody conjugated with a fluorescent tag is used and directed against the second reporter protein to monitor the level of expression of the second reporter. The antibody is incubated with the cells, excess antibody is washed off, and the fluorescence is monitored at a wavelength different from GFP. The ratio of GFP expression to second reporter expression is used as a measure to determine the degree of inhibition of expression of the target sequence. The cells are lysed, plasmid extracted, amplified in bacteria, and sequenced to identify the EGS or ribozyme associated with the cell population.

Transformation in Two Separate Plasmids

In another embodiment, two separate plasmids are used to transform *E. coli*. The first one encodes the fusion protein (target-GFP) and the second one encodes the second reporter and the targeting gene encoding a library of EGS or ribozymes. The plasmids encoding the EGS/ribozyme library are grown in bacteria and mixed plasmids prepared as described above.

A fixed concentration of the mixed plasmids (each encoding a separate EGS or ribozyme) is combined with a fixed concentration of the target plasmid (encoding the target-GFP fusion protein). The mixture is complexed with a commercially available preparation of lipid or calcium phosphate and transfected to cells plated in 96 wells. At the peak of expression of GFP, the levels of GFP-fluorescence and the level of expression of the second reporter are measured and the ratio of GFP expression to second reporter is used to determine the efficacy of EGS or ribozyme. The ratio of EGS to target can be altered to change the level of expression of the EGS or ribozyme over the target.

This method for identifying functional oligonucleotide molecules, especially EGSs with enhanced or optimal activity in inducing cleavage of an RNA molecule of interest by RNase P, will be further understood by reference to the following non-limiting examples.

EXAMPLE 4

Selecting Functional EGS from a Pool of EGS

A prokaryotic base vector including a fusion protein of CAT-β-galactosidase expressed dark blue colonies. A library of DNA encoding 55 EGS sequences complementary to the CAT gene was inserted into the targeting gene of the base vector.

Two libraries were made. The first library, Library A, encoded EGS followed by a T7 terminator. The second library encoded EGS followed by a self-cleaving hammerhead ribozyme to mature 3' end of the EGS. Expression in the second library was lower, presumably due to lower stability.

Library A was plated on X-gal plates. Light and dark blue colonies were counted. Light blue colonies were presumed to show EGS-mediated interference of CAT expression. Colonies grown from the EGS library provided approximately 5% light blue colonies, compared to less than 1% of light blue colonies on control plates (those colonies grown from libraries without EGS insertions). This total number of positives was consistent with two to three EGS sequences out of the original library being effective. Accordingly, a tight grouping of sequences was expected. Therefore, light blue colonies were picked and replated. The light blue color was preserved. Most of the light blue colonies were assayed for β-galactosidase activity and manifested an 80 to 90% inhibition of enzyme activity.

DNA from four of the light blue colonies was isolated and sequenced. Each colony encoded the same EGS. This EGS was inserted into the base vector. Approximately 90% inhibition of CAT activity was observed. Qualitatively, less inhibition was seen with the second library.

As a control, the converse experiment was performed. The EGS was removed from the base vector. Wild type levels of β-galactosidase expression were observed. These data indicates that functional EGS can be selected from a large pool. EGSs 1 and 2 (shown in Guerrier-Takeda, et al., *Proc. Natl. Acad. USA* 1997), previously identified functional EGS targeted to CAT RNA, show little or no activity in these assays.

Thirty-nine positives from Library A were selected through tertiary screening. DNA was prepared and sequenced. Only eight of the original 53 EGS sequences were found, with EGS number 52 recurring twenty three times. As a control, forty eight colonies were selected from Library A at random without regard to the expression level of β-galactosidase. In this random set, twenty eight EGS sequences were found, no one sequence recurring more than five times. Table 4 shows the distribution of the EGS sequences.

TABLE 4

Distribution of EGS Sequences.

| EGS | No. Found Randoms | No. Found Selected | EGS | No. Found Randoms | No. Found Selected |
|---|---|---|---|---|---|
| 1 | 0 | 0 | 29 | 0 | 0 |
| 2 | 1 | 0 | 30 | 0 | 0 |
| 3 | 1 | 0 | 31 | 1 | 3 |
| 4 | 0 | 0 | 32 | 0 | 0 |
| 5 | 0 | 0 | 33 | 1 | 0 |
| 6 | 0 | 0 | 34 | 3 | 0 |
| 7 | 0 | 0 | 35 | 1 | 1 |
| 8 | 0 | 1 | 36 | 1 | 5 |
| 9 | 1 | 0 | 37 | 1 | 0 |
| 10 | 0 | 0 | 38 | 2 | 0 |
| 11 | 2 | 0 | 39 | 0 | 0 |

TABLE 4-continued

Distribution of EGS Sequences.

| EGS | No. Found Randoms | No. Found Selected | EGS | No. Found Randoms | No. Found Selected |
|---|---|---|---|---|---|
| 12 | 3 | 0 | 40 | 1 | 0 |
| 13 | 0 | 3 | 41 | 0 | 0 |
| 14 | 3 | 0 | 42 | 0 | 0 |
| 15 | 0 | 0 | 43 | 4 | 0 |
| 16 | 0 | 0 | 44 | 0 | 0 |
| 17 | 0 | 0 | 45 | 2 | 0 |
| 18 | 2 | 0 | 46 | 0 | 0 |
| 19 | 1 | 0 | 47 | 0 | 0 |
| 20 | 2 | 3 | 48 | 1 | 0 |
| 21 | 5 | 1 | 49 | 0 | 0 |
| 22 | 0 | 0 | 50 | 2 | 0 |
| 23 | 1 | 0 | 51 | 0 | 0 |
| 24 | 1 | 0 | 52 | 2 | 23 |
| 25 | 1 | 0 | CAT1 | 1 | 0 |
| 26 | 1 | 0 | CAT2 | 0 | 0 |
| 27 | 0 | 0 | Total | 48 | 39 |
| 28 | 0 | 0 | | | |

Figure 9A:
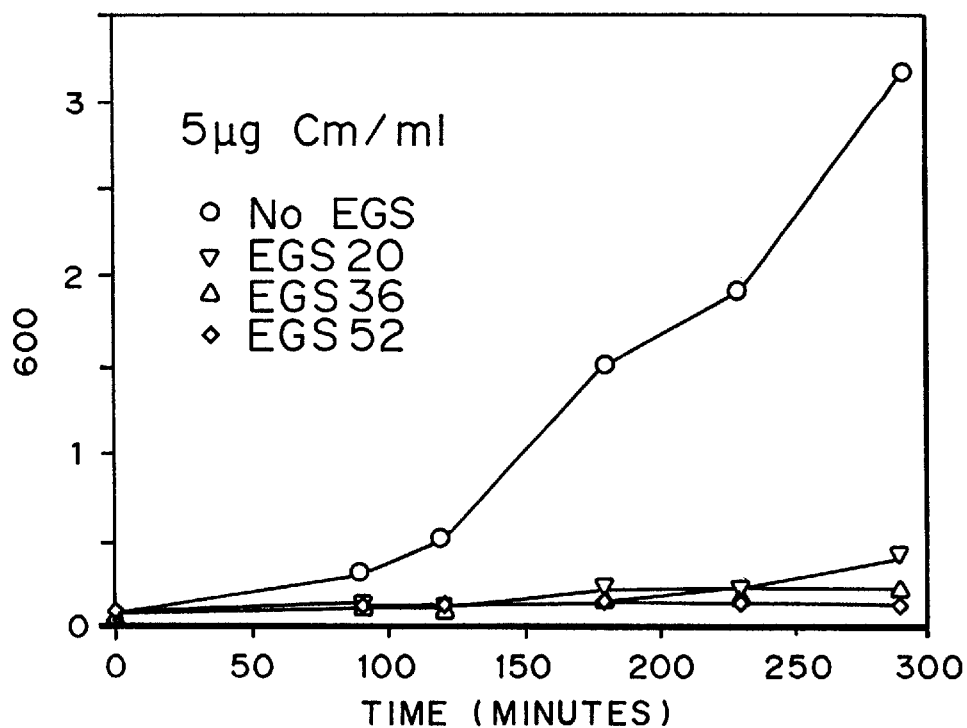
FIGS. 9A and 9B are graphs of cell culture density (A600) versus time (in minutes) of cells in the presence of 5 μg/ml chloramphenicol (FIG. 9A) or 25 μg/ml chloramphenicol (FIG. 9B). The cells contained a vector similar to the vector shown in FIG. 8 that did not encode an EGS (circles), encoded EGS 36 (triangles), encoded EGS 20 (inverted triangles), or encoded both EGS 52 (diamonds).
Figure 9B:
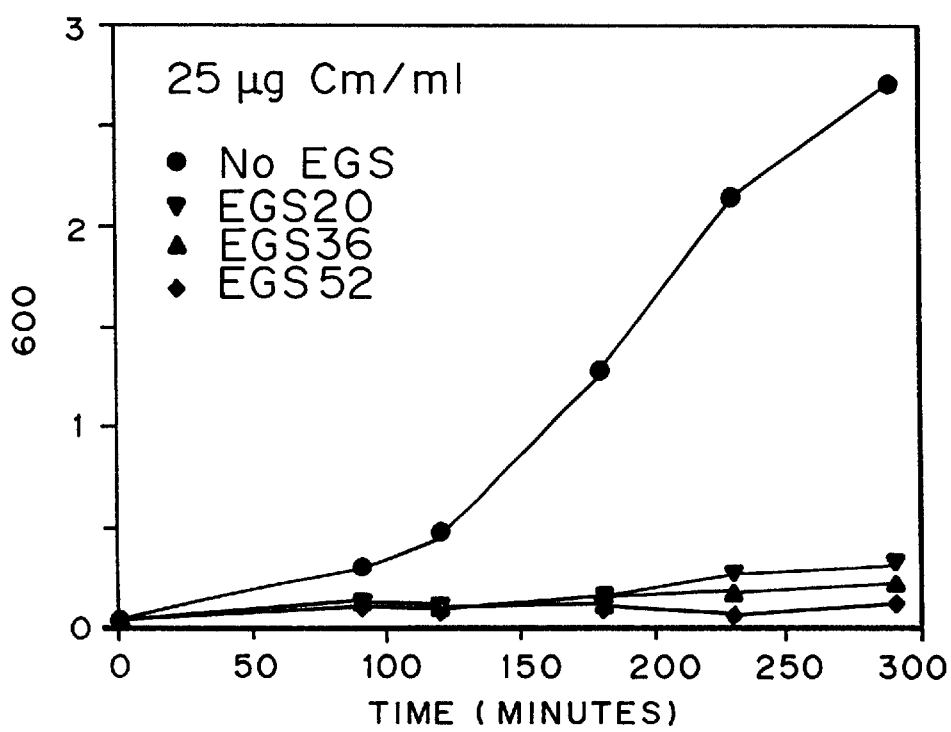

Therefore, by these criteria, EGS 52, EGS 36 and EGS 20 were identified as the most frequently selected EGS molecules. These same EGS molecules should be the most effective at inhibition of CAT gene expression. To test this, EGS 52, EGS 36, EGS 20 were expressed in cells expressing a CAT gene, and the cells were challenged with chloramphenicol. The results are shown in FIGS. 9A and 9B. All three of the selected EGS molecules have a significant effect on chloramphenicol resistance, while cells with a control plasmid lacking any EGS exhibit chloramphenicol resistance.

Figure 10:
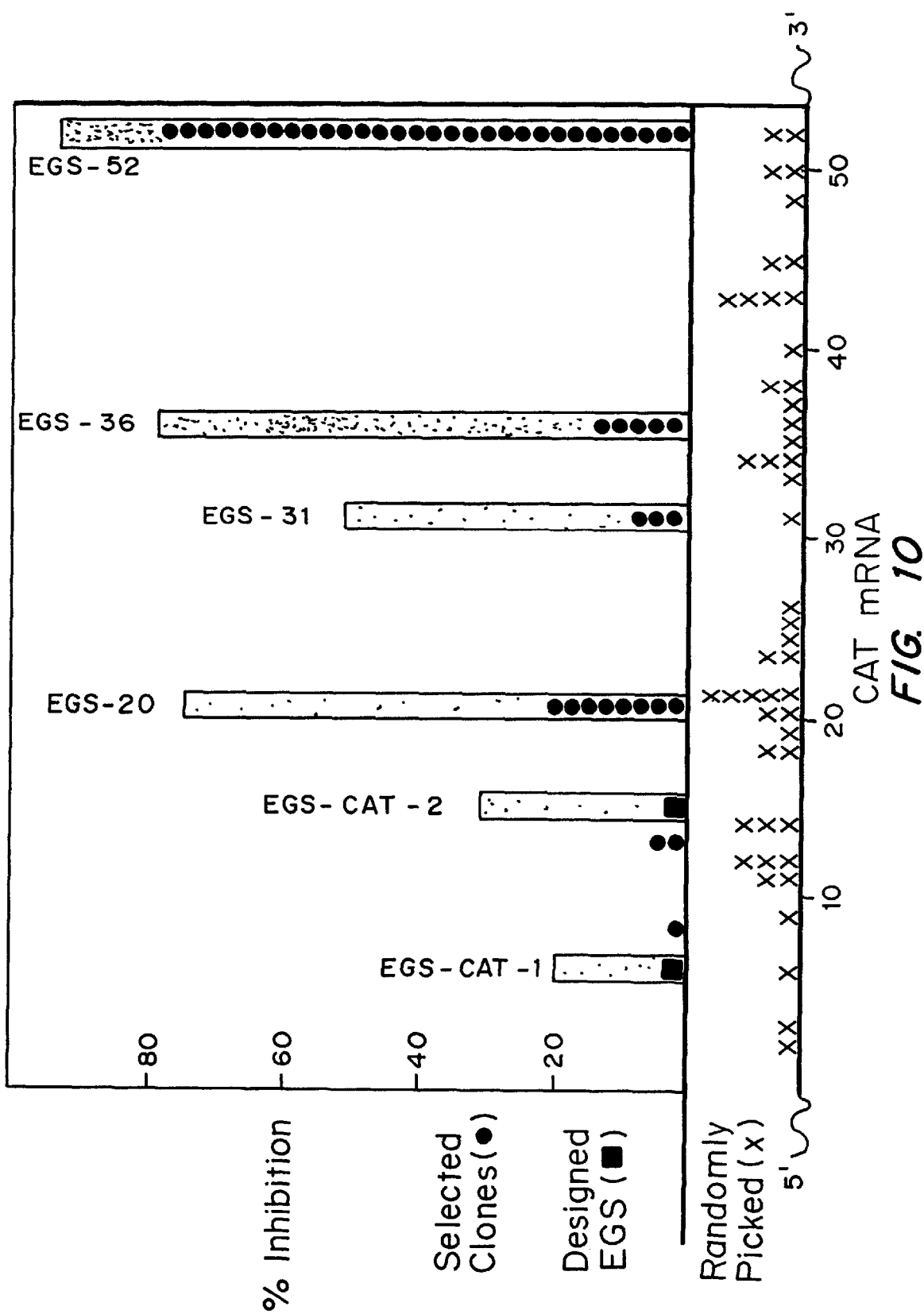
FIG. 10 is a graph of the percent inhibition of chloramphenicol acetyl transferase (CAT) activity by EGS-CAT-1, EGS-CAT-2, EGS-20, EGS-31, EGS-36, and EGS-52. Each X represents an EGS complementary to a specific sequence of the mRNA transcript of the CAT gene. The X's show that EGSs were recovered and that the library was represented in the experiment. The circles indicate the relative efficiency by which each EGS knocks down the expression of the targeted gene.

FIG. 10 further illustrates the data. Each X represents an EGS complementary to a specific sequence of the mRNA transcript of the CAT gene. The X's show that EGSs were recovered and that the library was represented in the experiment. The same EGS was found in a number of different clones that were chosen because of their light blue or off-white color. Equally important, most of the randomly picked EGSs from the non-indicator plate were different from the active EGSs selected from the indicator plate. Most potential loci in a mRNA molecule apparently were not accessible to the action of a complementary EGS. However, specific mRNA sites were identified that are accessible to an EGS.

The data in FIG. 10 also indicates the relative efficiency by which each EGS knocks down the expression of the targeted gene. With each set of circles, the observed inhibition of beta-galactosidase activity resulting from the specific EGS is shown. The most effective was EGS-52, which resulted in a 92% reduction of beta-galactosidase activity. Three other selected EGSs (EGS-31, EGS-20, and EGS-36) reduced beta-galactosidase activity by 20% and 30%, respectively.

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying genes affecting cell viability or phenotype, the method comprising mixing a library of external guide sequences targeting a plurality of sequences for cleavage by RNase P with cells, identifying cells with altered viability or phenotype, identifying the external guide sequences mixed with the cells having altered viability or phenotype, wherein genes corresponding to the external guide sequences mixed with the cells having altered viability or phenotype are genes affecting cell viability or phenotype.

2. The method of claim 1 wherein the external guide sequences target cleavage of an RNA molecule by a prokaryotic RNase P and the cells are bacterial cells.

3. The method of claim 1 wherein the external guide sequences target cleavage of an RNA molecule by eukaryotic RNase P and the cells are eukaryotic cells.

4. The method of claim 1 wherein the external guide sequences target cleavage of an RNA molecule by eukaryotic RNase P and the cells are fungal cells.

5. The method of claim 1 wherein the cells are selected from the group consisting of *Pseudomonas aeruginosa, Mycobacterium tuberculosis, Hemophilus influenzae, Staphylococcus aureus, Mycoplasma pneumoniae, Escherichia coli, Streptococcus pneumoniae, Neisseria gonorrhaoeae, Streptococcus viridans, Streptococcus pyogenes, Proteus mirabilis, Proteus vulgaris, Salmonella typhimurium, Shigella dysentereae, Clostridium difficile, Klebsiella pneumoniae, Candida albicans, Aspergillus flavus, Aspergillus fumagatus,* and *Histoplasmatus capsulatum.*

6. The method of claim 1 wherein the library is constructed to encompass all possible combinations of nucleotide sequences of a length effective to specifically direct cleavage by RNase P to any cleavage site in any RNA in a prokaryotic cell.

7. The method of claim 6 wherein the external guide sequences comprise $N_{10-13}$ oligomers.

8. The method of claim 1 wherein the external guide sequences comprise $N_{10-15}$ oligomers and the cells are fungi.

9. The method of claim 1, wherein the external guide sequences comprise $N_{10-18}$ oligomers and the cells are mammalian cells.

10. The method of claim 1 wherein the external guide sequences are in a vector which can be expressed and replicated in the cells.

11. The method of claim 10 wherein the vector comprises a reporter gene or selection gene which can be used to screen for cells harboring the vector or an external guide sequence inducing cleavage of an RNA encoded by a gene affecting cell viability or phenotype.

12. The method of claim 1 wherein the plurality of sequences is present in RNA selected from the group consisting of viral RNA, messenger RNA, transfer RNA, and ribosomal RNA.

13. The method of claim 11 further comprising selecting for cells containing an external guide sequence inducing cleavage of the RNA.

14. The method of claim 13 wherein the cells are first replicated and then exposed to an agent that affects cell viability or phenotype of cells only when an external guide sequence is expressed in the cells.

15. The method of claim 13 further comprising identifying the sequence of the external guide sequence affecting the viability or phenotype of the cells.

16. The method of claim 15 further comprising determining the sequence of the gene whose encoded RNA is cleaved by RNase P when targeted by the external guide sequence.

17. The method of claim 16 wherein the sequence of the gene is determined by analysis of multiple external guide sequences affecting the viability or phenotype of the cells when exposed to a defined agent.

* * * * *

SEQUENCE LISTING

```
<160> NUMBER OF SEQ ID NOS: 52

<210> SEQ ID NO: 1
<211> LENGTH: 19
<212> TYPE: RNA
<213> ORGANISM: Artificial Sequence
<220> FEATURE:
<223> OTHER INFORMATION: Description of Artificial Sequence: sample
      External Guide Sequence  (EGS)

<400> SEQUENCE: 1
ggauaagggc gacacacca                                                      19

<210> SEQ ID NO: 2
<211> LENGTH: 22
<212> TYPE: RNA
<213> ORGANISM: Artificial Sequence
<220> FEATURE:
<223> OTHER INFORMATION: Description of Artificial Sequence: sample
      target mRNA

<400> SEQUENCE: 2
uuccgugucg cccuuauucc cu                                                  22

<210> SEQ ID NO: 3
<211> LENGTH: 134
<212> TYPE: DNA
<213> ORGANISM: Artificial Sequence
<220> FEATURE:
<221> NAME/KEY: promoter
<222> LOCATION: (8)..(53)
<223> OTHER INFORMATION: C-pBAD promoter
```

```
<220> FEATURE:
<221> NAME/KEY: misc_feature
<222> LOCATION: (56)..(73)
<223> OTHER INFORMATION: External Guide Sequence
<220> FEATURE:
<221> NAME/KEY: terminator
<222> LOCATION: (74)..(113)
<223> OTHER INFORMATION: T7e Terminator
<220> FEATURE:
<223> OTHER INFORMATION: Description of Artificial Sequence: Insert for
      Making ARA-N11 Library
<220> FEATURE:
<221> NAME/KEY: misc_feature
<222> LOCATION: (55)..(65)
<223> OTHER INFORMATION: N=A, G, C, or T, preferably A and G

<400> SEQUENCE: 3
gattagcgga tcctacctga cgcttttat cgcaactctc tactgttctc catannnnnn    60
nnnnnccacc aaaatgtaat cacactggct cccttcgggt tgggcctttc tgcgaagctt  120
ggctgtaaca cgga                                                    134

<210> SEQ ID NO: 4
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
tacgacgcga c                                                        11

<210> SEQ ID NO: 5
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
cgcacgcgat g                                                        11

<210> SEQ ID NO: 6
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
tacaactgcc c                                                        11

<210> SEQ ID NO: 7
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gcttcgaaga c                                                        11

<210> SEQ ID NO: 8
<211> LENGTH: 11
```

<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
tggcgcgacg a                                                              11

<210> SEQ ID NO: 9
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
atctcagaac c                                                              11

<210> SEQ ID NO: 10
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
cgcgatgact c                                                              11

<210> SEQ ID NO: 11
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
gtgatgcggc g                                                              11

<210> SEQ ID NO: 12
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
gtgtctgttg c                                                              11

<210> SEQ ID NO: 13
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
ctagtgacgc g                                                              11

<210> SEQ ID NO: 14
<211> LENGTH: 11
<212> TYPE: DNA

```
<213> ORGANISM: Artificial Sequence
<220> FEATURE:
<223> OTHER INFORMATION: Description of Artificial Sequence:
      oligonucleotide

<400> SEQUENCE: 14
tgtttggcga t                                                               11

<210> SEQ ID NO: 15
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
gcgatagcta a                                                               11

<210> SEQ ID NO: 16
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
agatgacgtg g                                                               11

<210> SEQ ID NO: 17
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
cagccattca a                                                               11

<210> SEQ ID NO: 18
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
gcgaccgtgg c                                                               11

<210> SEQ ID NO: 19
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
ccgacgacag c                                                               11

<210> SEQ ID NO: 20
<211> LENGTH: 11
<212> TYPE: DNA
<213> ORGANISM: Artificial Sequence
```

```
<220> FEATURE:
<223> OTHER INFORMATION: Description of Artificial Sequence:
      oligonucleotide

<400> SEQUENCE: 20
ccgacgacag c                                                          11

<210> SEQ ID NO: 21
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
ccataatatc t                                                          11

<210> SEQ ID NO: 22
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
gtgtgtaagc g                                                          11

<210> SEQ ID NO: 23
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
tcctggagaa g                                                          11

<210> SEQ ID NO: 24
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
catcctctta c                                                          11

<210> SEQ ID NO: 25
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
ctatccaaca g                                                          11

<210> SEQ ID NO: 26
<211> LENGTH: 11
<212> TYPE: DNA
<213> ORGANISM: Artificial Sequence
<220> FEATURE:
```

<223> OTHER INFORMATION: Description of Artificial Sequence:
      oligonucleotide

<400> SEQUENCE: 26
cgtaagcgac g                                                          11

<210> SEQ ID NO: 27
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
gacgtgacga a                                                          11

<210> SEQ ID NO: 28
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
ccgaatagtg t                                                          11

<210> SEQ ID NO: 29
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
gacgacgagg c                                                          11

<210> SEQ ID NO: 30
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
cagcttttgc n                                                          11

<210> SEQ ID NO: 31
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
tgccaactta c                                                          11

<210> SEQ ID NO: 32
<211> LENGTH: 11
<212> TYPE: DNA
<213> ORGANISM: Artificial Sequence
<220> FEATURE:
<223> OTHER INFORMATION: Description of Artificial Sequence:

oligonucleotide

<400> SEQUENCE: 32
gtagagcgac g                                                           11

<210> SEQ ID NO: 33
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
cacgacgagg c                                                           11

<210> SEQ ID NO: 34
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
tcagccaatg c                                                           11

<210> SEQ ID NO: 35
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
ggatgtgagc c                                                           11

<210> SEQ ID NO: 36
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
gaagcgttca g                                                           11

<210> SEQ ID NO: 37
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37
catttaacaa c                                                           11

<210> SEQ ID NO: 38
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

```
<400> SEQUENCE: 38
tgatagtttc c                                                    11

<210> SEQ ID NO: 39
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
cataacatcc t                                                    11

<210> SEQ ID NO: 40
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40
ctaacagcca tt                                                   12

<210> SEQ ID NO: 41
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
ctggcttatc cc                                                   12

<210> SEQ ID NO: 42
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 42
cagccactgc ct                                                   12

<210> SEQ ID NO: 43
<211> LENGTH: 13
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 43
acaactgcca att                                                  13

<210> SEQ ID NO: 44
<211> LENGTH: 12
<212> TYPE: DNA
<213> ORGANISM: Artificial Sequence
<220> FEATURE:
<223> OTHER INFORMATION: Description of Artificial Sequence:
      oligonucleotide
```

-continued

```
<400> SEQUENCE: 44
ccagcatgta tc                                                          12

<210> SEQ ID NO: 45
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 45
gcgatagacc aa                                                          12

<210> SEQ ID NO: 46
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 46
caactgccca ac                                                          12

<210> SEQ ID NO: 47
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 47
caatgacgcg aa                                                          12

<210> SEQ ID NO: 48
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 48
gcttagctcg ta                                                          12

<210> SEQ ID NO: 49
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 49
cggcgatgcg gt                                                          12

<210> SEQ ID NO: 50
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 50
```

-continued

```
gcctaaccgg cg                                                                12

<210> SEQ ID NO: 51
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 51
cgcgacggat gg                                                                12

<210> SEQ ID NO: 52
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 52
agcagagcac ag                                                                12
```